(12) United States Patent
Judson

(10) Patent No.: US 10,828,423 B2
(45) Date of Patent: Nov. 10, 2020

(54) DISPENSING DEVICE WITH DRIVE MECHANISM HAVING CONVERGING RAMPS

(71) Applicant: Eli Lilly and Company, Indianapolis, IN (US)

(72) Inventor: Jared Alden Judson, Medford, MA (US)

(73) Assignee: Eli Lilly and Company, Indianapolis, IN (US)

( * ) Notice: Subject to any disclaimer, the term of this patent is extended or adjusted under 35 U.S.C. 154(b) by 410 days.

(21) Appl. No.: 15/554,441

(22) PCT Filed: Mar. 10, 2016

(86) PCT No.: PCT/US2016/021647
§ 371 (c)(1),
(2) Date: Aug. 30, 2017

(87) PCT Pub. No.: WO2016/149014
PCT Pub. Date: Sep. 22, 2016

(65) Prior Publication Data
US 2018/0064882 A1 Mar. 8, 2018

Related U.S. Application Data

(60) Provisional application No. 62/134,865, filed on Mar. 18, 2015.

(51) Int. Cl.
*A61M 5/315* (2006.01)
*A61M 5/24* (2006.01)
(Continued)

(52) U.S. Cl.
CPC .......... *A61M 5/31578* (2013.01); *A61M 5/20* (2013.01); *A61M 5/24* (2013.01);
(Continued)

(58) Field of Classification Search
CPC ............ A61M 5/20; A61M 5/24; A61M 5/28; A61M 5/31511; A61M 5/31565; A61M 5/31578; G02F 1/1335; G02F 1/13363
See application file for complete search history.

(56) References Cited

U.S. PATENT DOCUMENTS

2013/0053790 A1* 2/2013 Karlsson ............. A61M 5/2033
604/48

FOREIGN PATENT DOCUMENTS

EP 2438946 4/2012
WO 2003/080160 10/2003
(Continued)

OTHER PUBLICATIONS

Patent Cooperation Treaty International Search Report and Written Opinion of the International Searching Authority pertaining to International Application No. PCT/US2016/021647; dated Jun. 29, 2016; 6 pages; European Patent Office.

*Primary Examiner* — Brandy S Lee
(74) *Attorney, Agent, or Firm* — Jonathan Anderson

(57) ABSTRACT

A dispensing device for dispensing medication from a medication container. The dispensing device includes a housing, a drive member engageable with the medication container, at least one first ramp surface fixed relative to the housing, a driver movable within the housing to move the drive member for forcing medication from the medication container, the driver including at least one second ramp surface, and a plunger including at least one push module movable relative to the housing from a ready position to a plunged position. The at least one first ramp surface and the at least one second ramp surface have a complementary configuration to cause the driver to be moved to force medication from the medication container by a driving force applied to the at least one second ramp surface by the at least one push module as the at least one push module simulta- (Continued)

neously engages both the at least one first ramp surface and the at least one second ramp surface during movement of the plunger from a ready position to a plunged position.

27 Claims, 31 Drawing Sheets

(51) Int. Cl.
*A61M 5/28* (2006.01)
*A61M 5/20* (2006.01)

(52) U.S. Cl.
CPC .......... *A61M 5/28* (2013.01); *A61M 5/31511* (2013.01); *A61M 5/31565* (2013.01)

(56) References Cited

FOREIGN PATENT DOCUMENTS

| WO | 2005/097233 | 10/2005 |
| WO | 2005/097240 | 10/2005 |
| WO | 2015007812 | 1/2015 |
| WO | 2015/017550 | 2/2015 |

\* cited by examiner

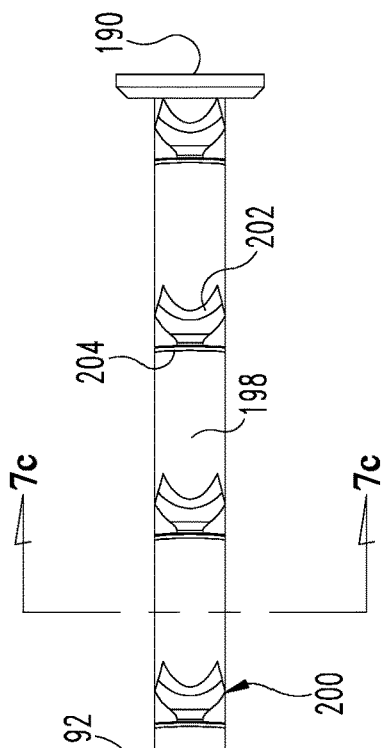
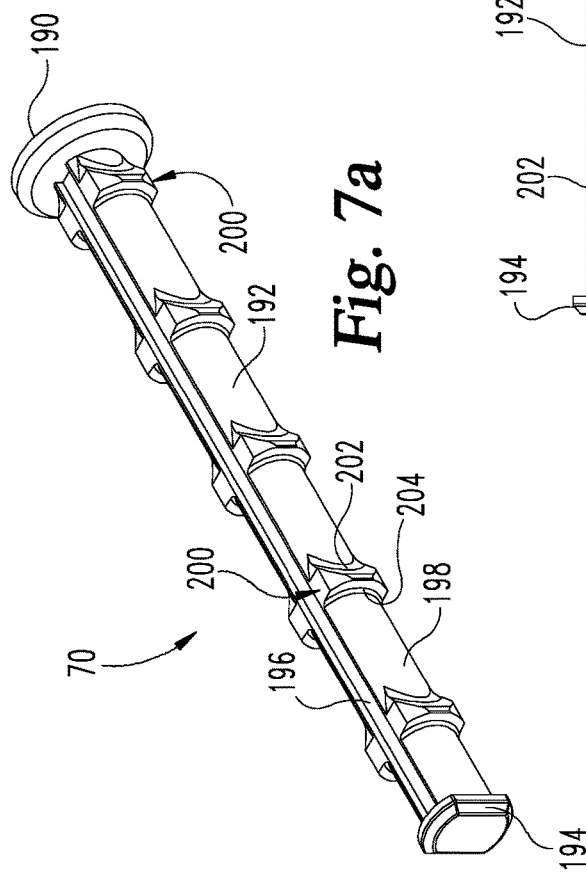
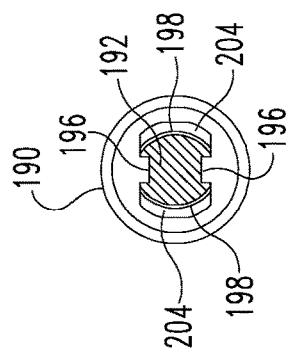

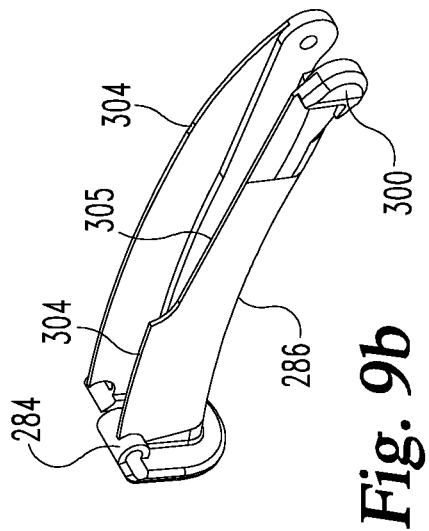
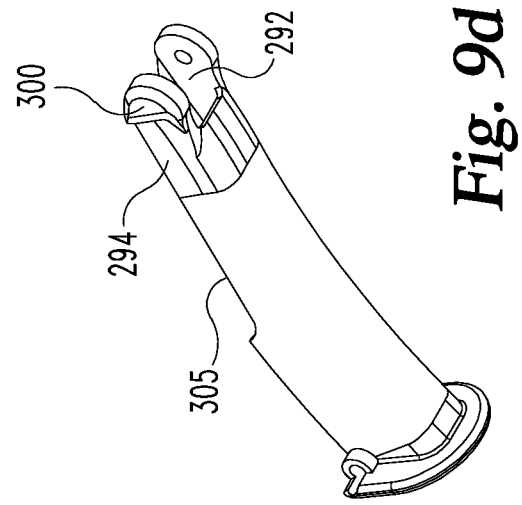
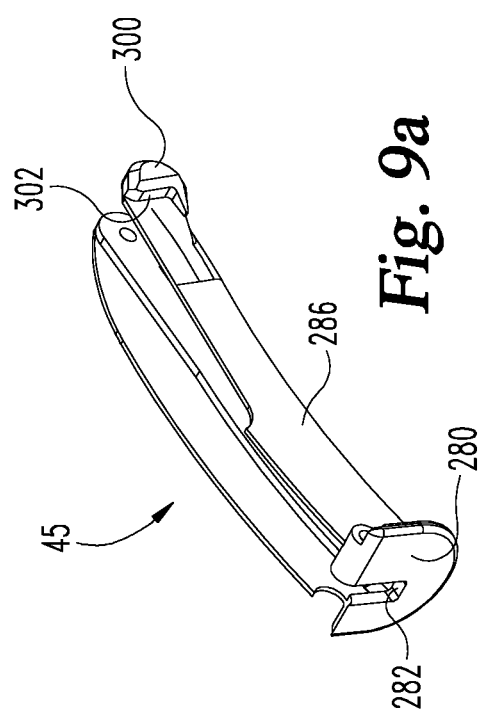
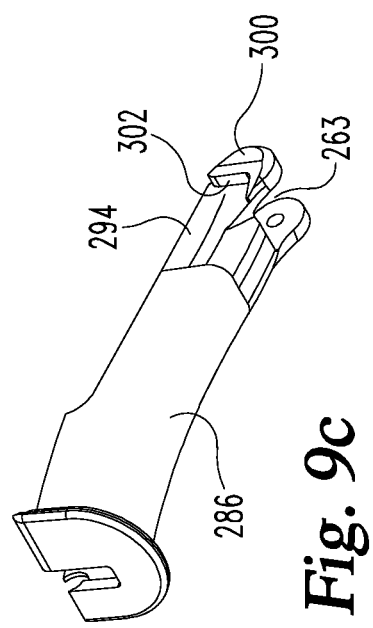

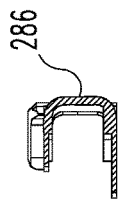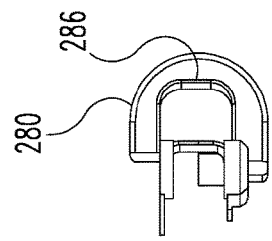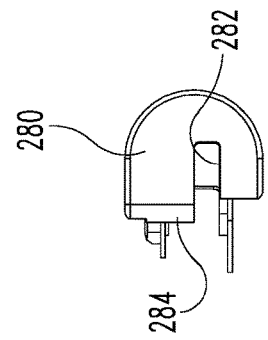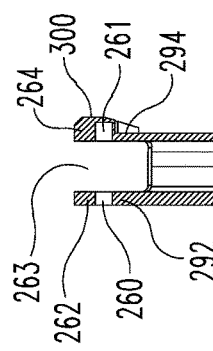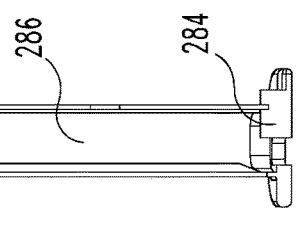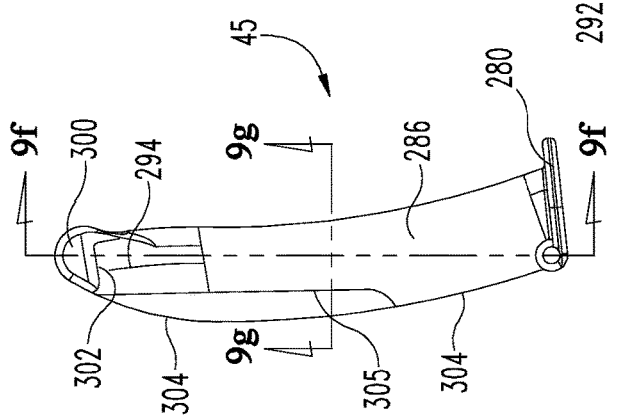

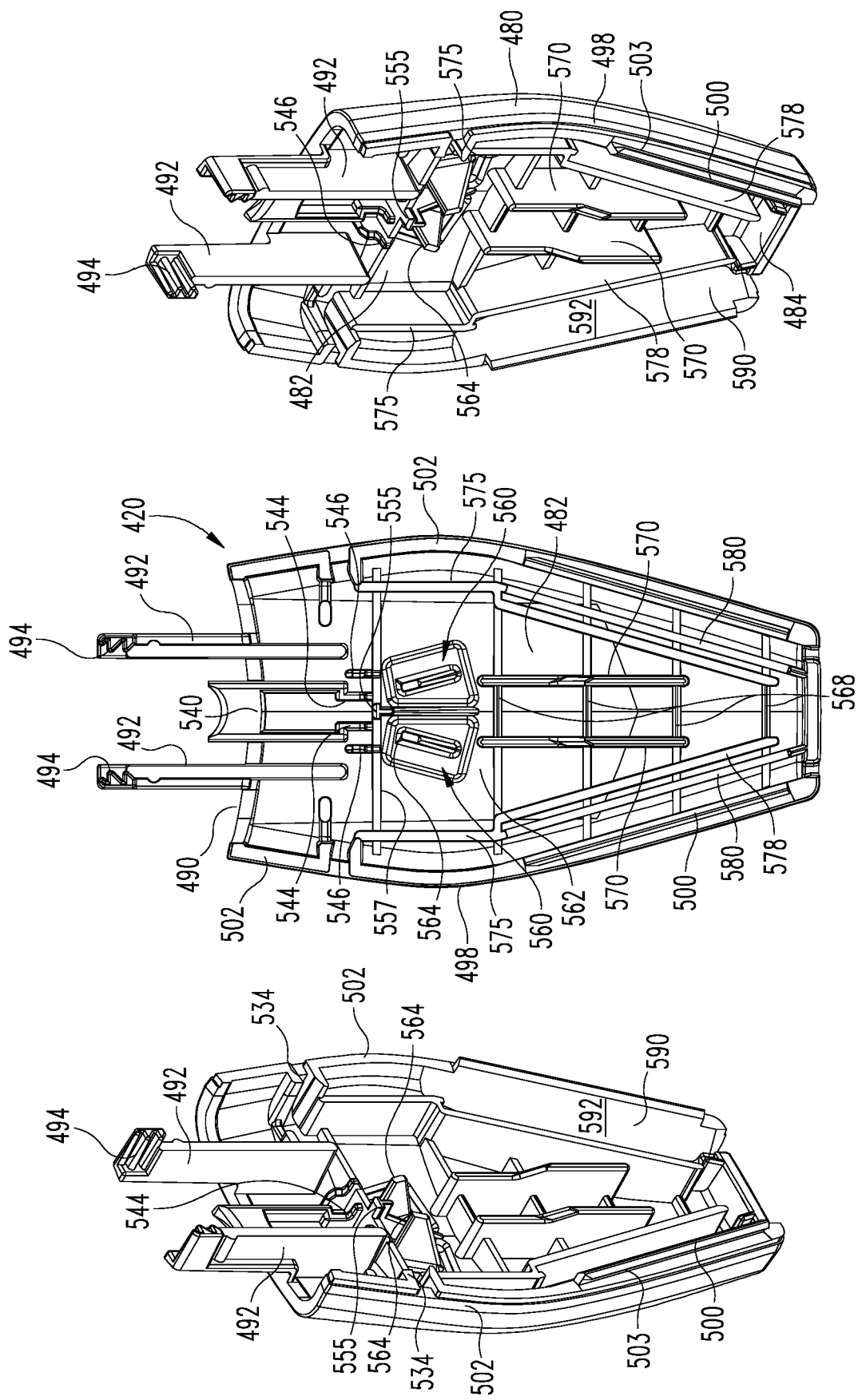

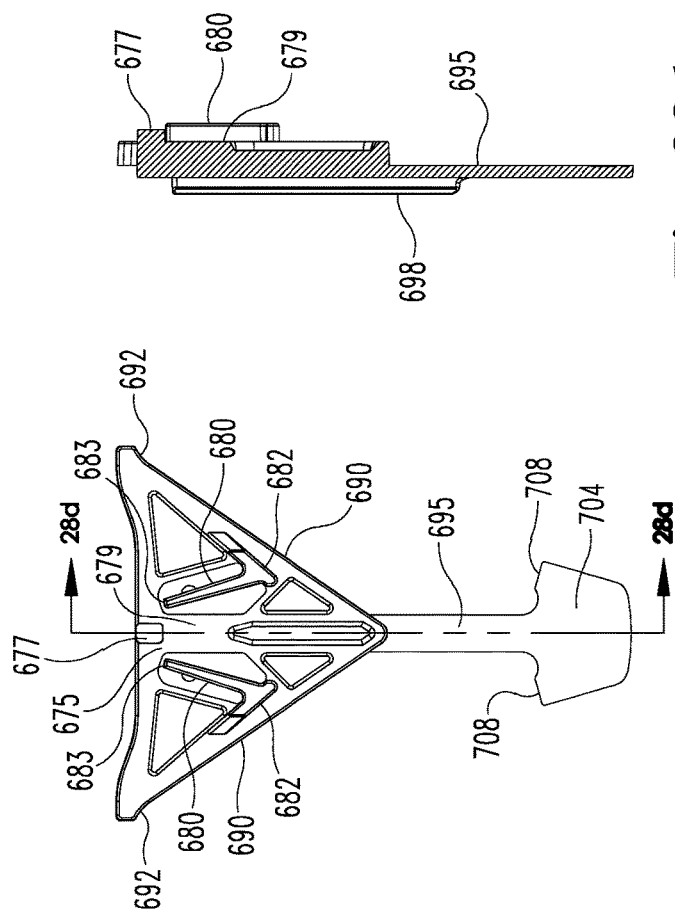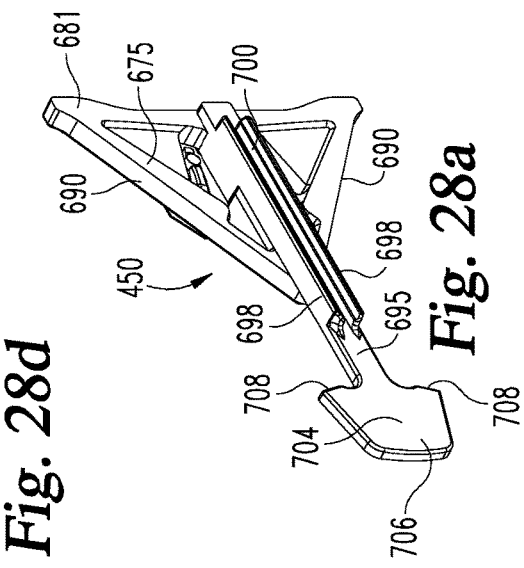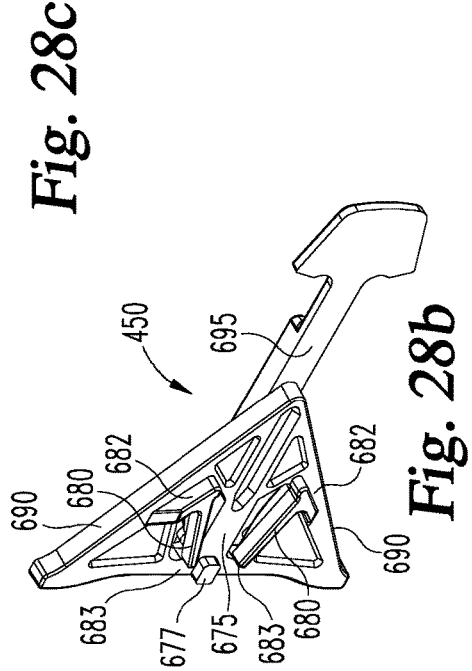

DISPENSING DEVICE WITH DRIVE MECHANISM HAVING CONVERGING RAMPS

BACKGROUND OF THE INVENTION

The present invention pertains to dispensing devices, and, in particular, to a medication dispensing device having a drive mechanism that provides a mechanical advantage.

Patients suffering from a number of different diseases frequently must inject themselves with medication. To allow a person to conveniently and accurately self-administer medicine, a variety of devices broadly known as injector pens or injection pens have been developed. Generally, these pens are equipped with a cartridge including a piston or plunger and containing a multi-dose quantity of liquid medication. A drive member, extending from within a base of the injector pen and operably connected with typically more rearward mechanisms of the pen that control drive member motion, is movable forward to advance the plunger in the cartridge in such a manner to dispense the contained medication from an outlet at the opposite cartridge end, typically through a needle that penetrates a stopper at that opposite end. In disposable pens, after a pen has been utilized to exhaust the supply of medication within the cartridge, the entire pen is discarded by a user, who then begins using a new replacement pen.

Injection pens typically are designed to provide a mechanical advantage intended to amplify user-applied forces to make it easier for users to dispense medication from the pens. This mechanical advantage may be particularly important where the medication is highly viscous, or where the typical user may be weak.

A variety of injection devices that provide a mechanical advantage are known. While useful, many such devices suffer from one or more shortcomings. For example, some devices provide mechanical advantage using gears and racks which may complicate manufacture as well as impact the robustness of the device.

Thus, it would be desirable to provide a dispensing device having a mechanical advantage that solves one or more of the above or other shortcomings of the prior art.

BRIEF SUMMARY OF THE INVENTION

In one form thereof, the present invention provides a dispensing device for dispensing medication from a medication container, the dispensing device including a housing, a drive member extending within the housing and engageable with the medication container, at least one first ramp surface fixed relative to the housing, a driver movable within the housing from a first position to a second position to move the drive member for forcing medication from the medication container, the driver including at least one second ramp surface, and a plunger including at least one push module movable relative to the housing from a ready position to a plunged position. The at least one first ramp surface and the at least one second ramp surface have a complementary configuration to cause the driver to be moved toward the second position by a driving force applied to the at least one second ramp surface by the at least one push module as the at least one push module simultaneously engages both the at least one first ramp surface and the at least one second ramp surface during movement from the ready position to the plunged position, the complementary configuration including converging regions of the at least one first ramp surface and the at least one second ramp surface sized and positioned to prevent the at least one push module from continuing to move toward the plunged position until the driver is moved toward the second position by the at least one push module.

In another form thereof, the present invention provides a dispensing device including a housing, a container of medication including a piston and an outlet, a drive member having an end within the container for advancing the piston, a driver movable within the housing to move the drive member to advance the container piston to force a dose of medication through the outlet, a manually operable plunger including a user pushable element and at least one push module, the manually operable plunger including a user pushable element disposed outside of the housing, the at least one push module movable within the housing from a ready position to a plunged position when the user pushable element is operated, and converging ramp means for converting motion of the at least one push module toward the plunged position into driver movement for advancing the container piston.

One advantage of the present invention is that a dispensing device can be provided which furnishes a mechanical advantage in an easy to use device configuration.

Another advantage of the present invention is that a dispensing device can be provided that does not require interfitting racks and pinions.

Another advantage of the present invention is that a dispensing device can be provided which allows delivery of multiple doses of even viscous materials.

Still another advantage of the present invention is that a dispensing device platform can be provided which allows different devices to be manufactured to deliver different dose amounts by merely changing a ramp angle and a ratchet spacing.

BRIEF DESCRIPTION OF THE DRAWINGS

The above-mentioned and other advantages and objects of this invention, and the manner of attaining them, will become more apparent, and the invention itself will be better understood by reference to the following description of embodiments of the invention taking in conjunction with the accompanying drawings, wherein:

FIGS. 7a, 7b and 7c are a perspective view, a side view, and a cross-sectional view taken along line 7c-7c in FIG. 7b, respectively, of a drive member of the device of FIG. 1;

FIGS. 9a, 9b, 9c, 9d, 9e, 9f, 9g, 9h, 9i and 9j four different perspective views, a front view, a cross-sectional view taken along line 9f-9f of FIG. 9e, a cross-sectional view taken along line 9g-9g of FIG. 9e, a side view, a bottom view and a top view, respectively, of a plunger arm of the device of FIG. 1;

FIGS. 24a, 24b, 24c, 24d, 24e and 24f are a front view, a left perspective view, a right perspective view, a side view, a top view and a bottom view, respectively, of the distal housing back piece of the device of FIG. 17;

FIGS. 28a, 28b, 28c and 28d are a front perspective view, a back perspective view, a back view, and a cross-sectional view taken along line 28d-28d of FIG. 28c, respectively, of a driver of the device of FIG. 17;

Figure 2:
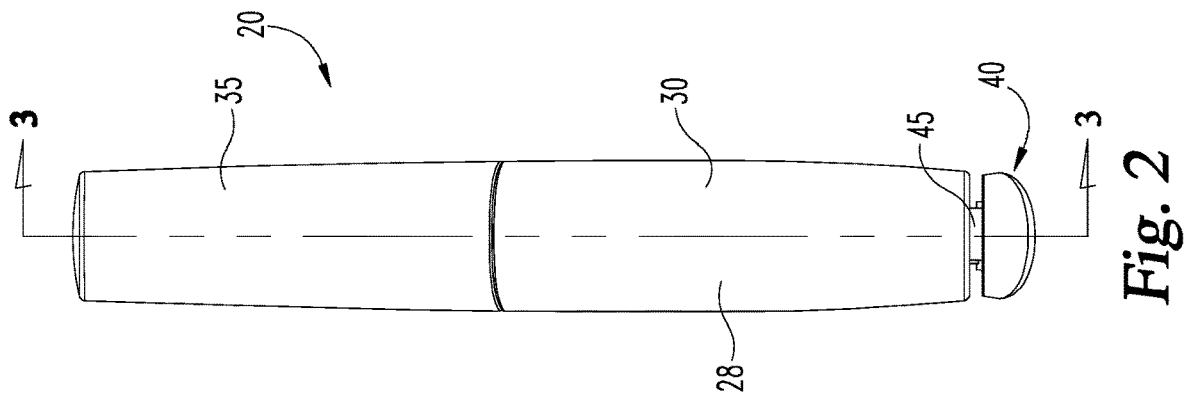
FIG. 2 is a side view of the medication dispensing device of FIG. 1.

Corresponding reference characters indicate corresponding parts throughout the several views. Although the drawings represent embodiments of the present invention, the drawings are not necessarily to scale, and certain features may be exaggerated or omitted in some of the drawings in order to better illustrate and explain the present invention.

DETAILED DESCRIPTION OF THE INVENTION

Referring now to FIGS. 1-5, there are shown various views of a medication dispensing device or apparatus that advantageously has been equipped with a drive mechanism that provides a mechanical advantage. The mechanical advantage is achieved with converging ramp surfaces, such as at least one ramp surface associated with a driver and at least one ramp surface associated with a housing, that are operatively engaged by a plunger portion for converting plunger motion of a first distance relative to the housing into a motion of an output drive member of a second distance less than the first distance.

The shown device, generally designated 20, is generally configured as a pen-shaped injector having an enlarged, grippable housing, although different device configurations can be equipped with the drive mechanism. The references in this application to front, side, and back, as well as to top and bottom, are all taken from the perspective of a viewer of device 20 as arranged in FIG. 1, and the references to distal and proximal are with respect to the end from which dispensing occurs in the shown embodiment, and all of these references are not intended to be limiting. The device 20 can be and normally will be arranged differently from that shown in the Figures, such as pointing down, during its operation to dispense a dose of medication.

Dispensing device 20 includes a housing, generally designated 25, in which other portions of the device are protectively encased. The housing 25, in the shown embodiment, also contains the medication to be dispensed by device 20. The housing alternatively could have the medication container directly attached thereto.

Figure 3:
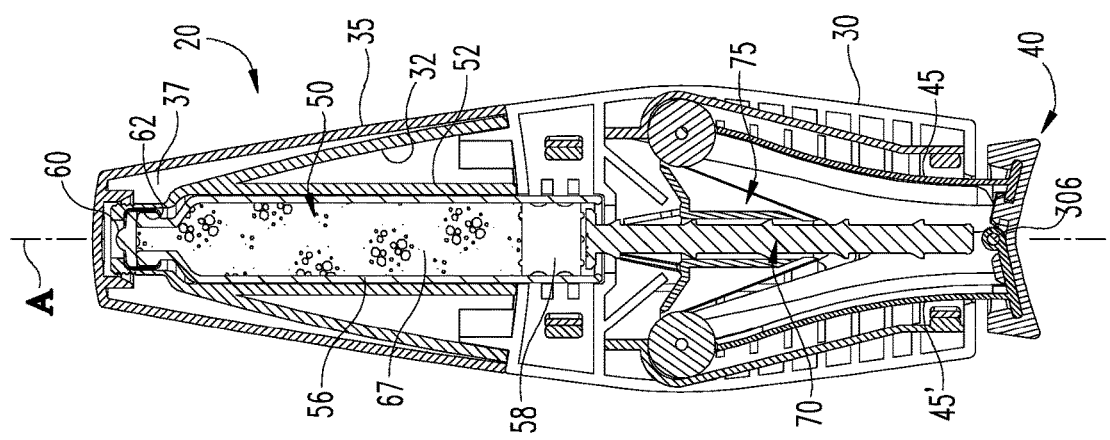
FIG. 3 is a front view in longitudinal cross-section taken along line 3-3 in FIG. 2 of the device of FIG. 1 prior to being used to deliver a dose.
Figures 6A, 6B, 6C, 6D, 6E, 6F:
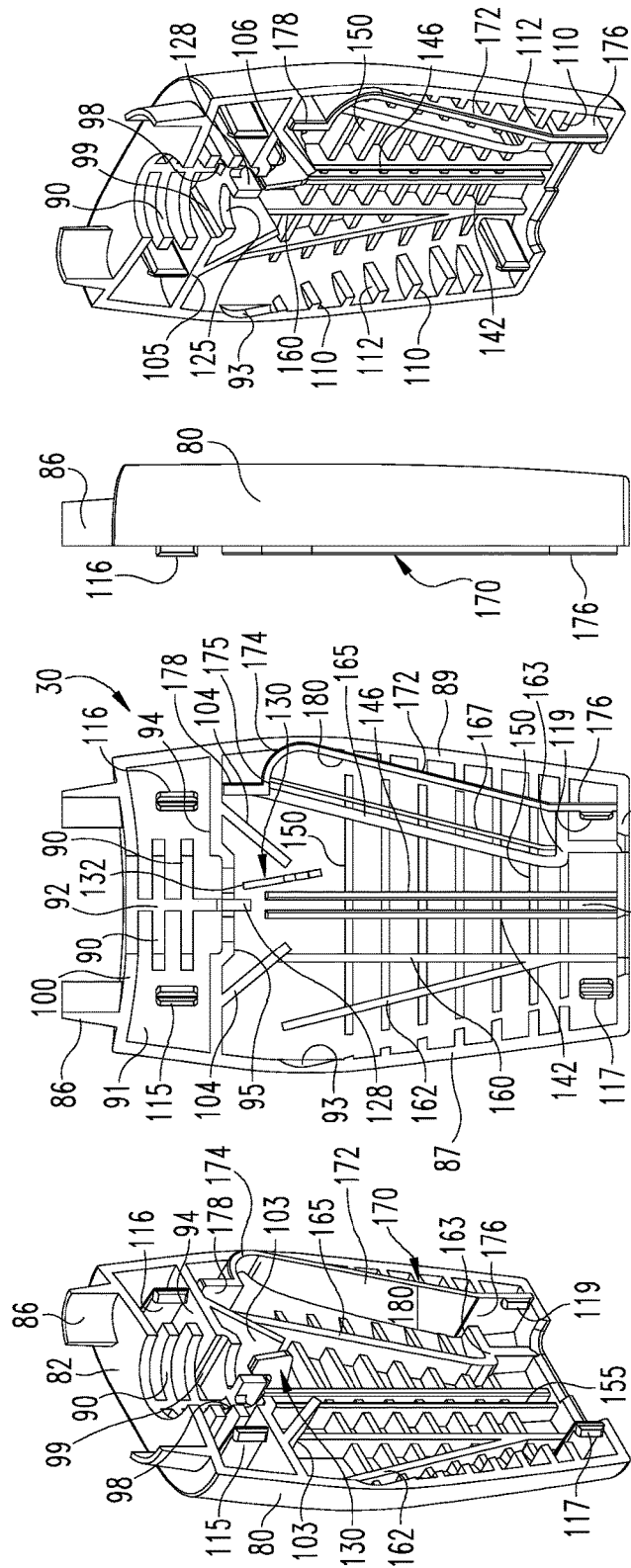
FIGS. 6a, 6b, 6c, 6d, 6e and 6f are a front view, a left perspective view, a right perspective view, a side view, a top view, and a bottom view, respectively, of the back distal housing half of the device of FIG. 1.
Figure 8C:
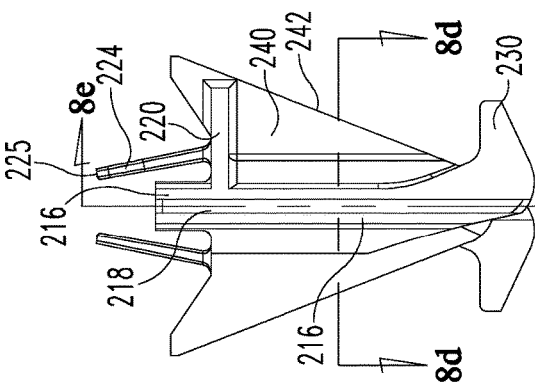
FIGS. 8a, 8b, 8c, 8d, 8e, 8f, 8g and 8h are a top perspective view, a bottom perspective view, a front view, a cross-sectional view taken along line 8d-8d of FIG. 8c, a cross-sectional view taken along line 8e-8e of FIG. 8c, a side view, a top view and a bottom view, respectively, of a driver of the device of FIG. 1.
Figure 8H:
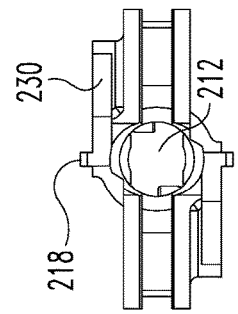
Figure 8D:
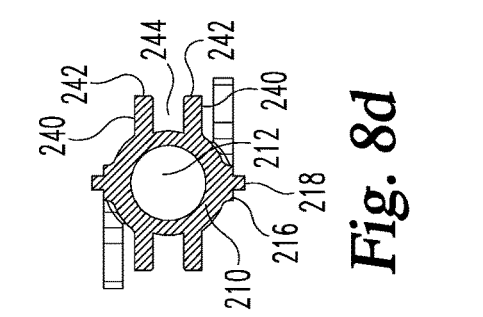
Figure 8F:
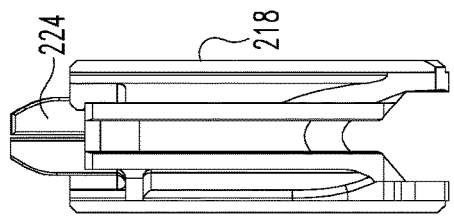
Figure 8B:
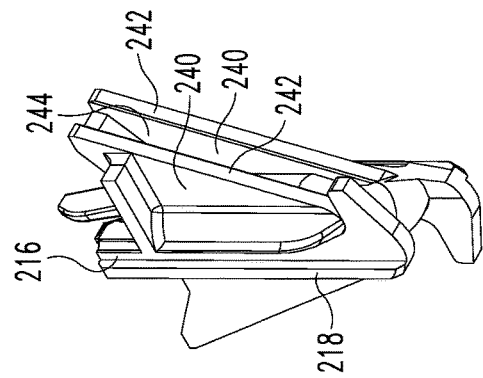
Figure 8G:
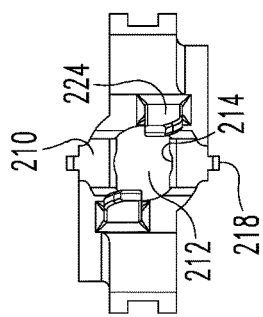
Figure 8A:
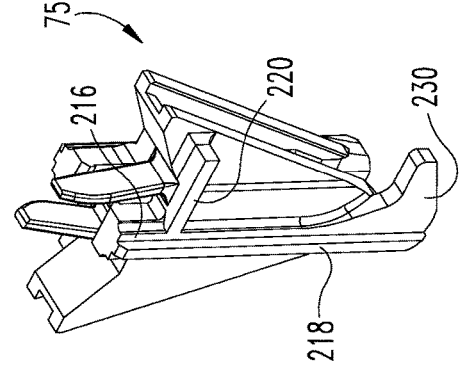
Figure 8E:
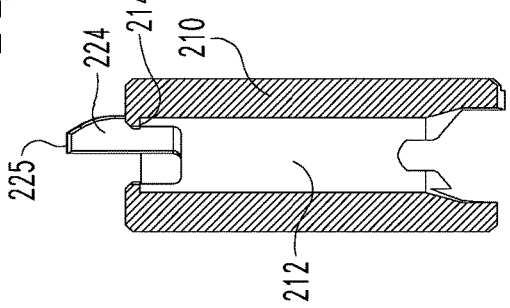

Housing 25 is formed by two mating pieces 28 and 30 and a cartridge retainer 32 that is securely attached, via an applied adhesive, to projecting flanges 86', 86 of housing pieces 28 and 30. Mating housing pieces 28 and 30 are identically structured and each forms half of the distal portion of housing 25. The cross-sectional view of FIG. 3 is taken along the plane at which the outer shells of housing pieces 28 and 30 meet or come together when assembled, which is the reason the distal housing portion in FIG. 3 is shown not being in cross section except for those regions of each of pieces 28 and 30 that extend through and are cut by that plane, which extending regions of piece 30 are further visible in FIG. 6d. The housing could be differently formed, with a different number of parts, within the scope of the invention, but the shown design facilitates assembly.

Figure 1:
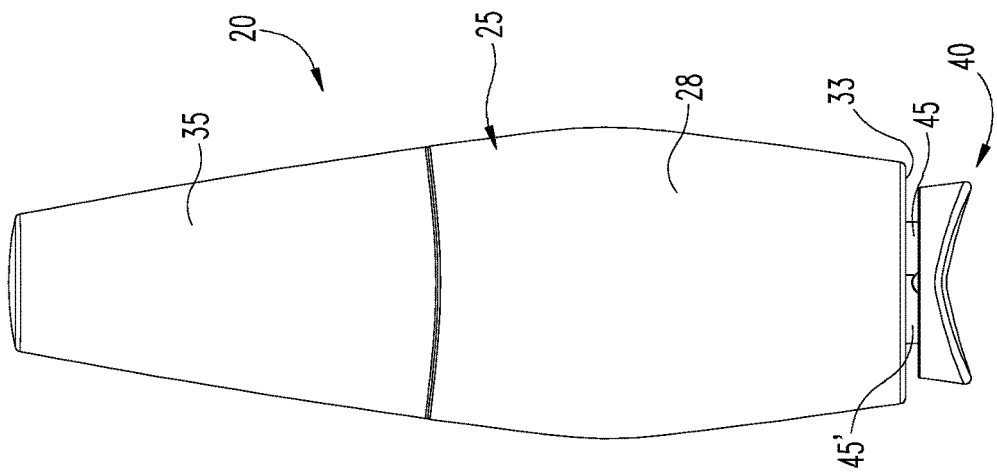
FIG. 1 is a front view of a first embodiment of a medication dispensing device that is equipped with a mechanical-advantage-providing drive mechanism that utilizes converging ramps.

A cap 35 is shown in FIGS. 1-3 mounted to housing 25 such that its interior hollow 37 fits over cartridge retainer 32. Cap 35 has an outer shape that continues the contour of the outer periphery of mated housing pieces 28, 30. Cap 35 is releaseably secured to housing 25 via detents 39 on opposite sides of retainer 32 which snap fit with cooperating indents (not shown) provided on the interior surface of cap 35. A user pulling cap 35 axially away from the housing can overcome the detent connection to allow removal of cap 35 for further use of device 20.

Housing 25 is injected molded from a durable, opaque plastic material such as acrylonitrile butadiene styrene. Slot-shaped windows 34 provided through both the front and rear faces of retainer 32 above detents 39 allow visibility of the medication contents of the device, when the cap is removed, but such windows may be eliminated if retainer 32 were formed of a transparent material.

A plunger button 40 of device 20 is located outside of the housing 25 below or distally of the housing distal end 33. A pair of plunger arms 45, 45' extends upward from button 40 and into the interior of housing 25. Button 40 is the portion of the drive mechanism intended to be accessible externally of the housing and physically contacted by the user during dose preparation and dose dispensing. Each of plunger arm 45, 45' includes at its proximal end within the housing 25 a push module used to transfer force to a driver 75.

Figure 4:
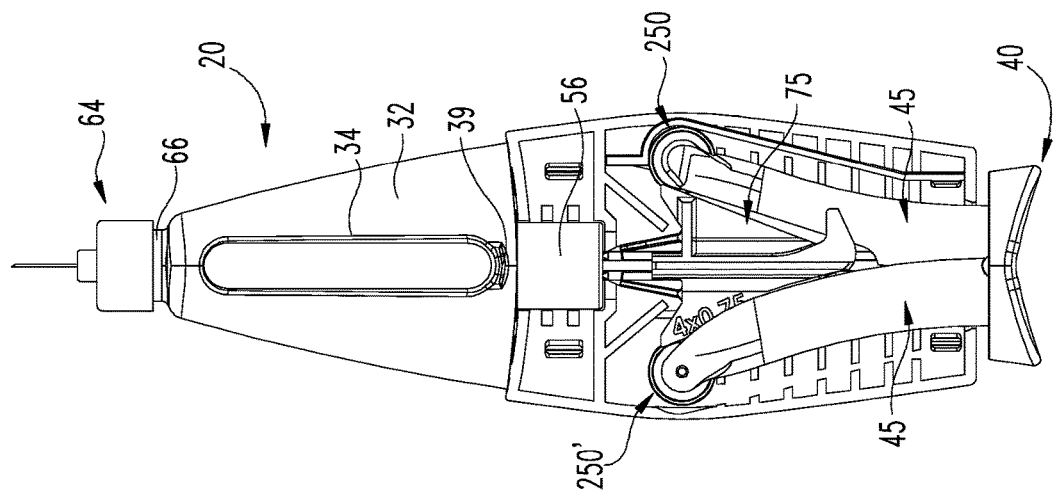
FIG. 4 is a front view of the medication dispensing device of FIG. 1 after the cap has been taken away and with a front distal housing piece removed, and equipped with an injection needle, prior to being used to deliver a dose.

As shown in FIGS. 3 and 4, the proximal portion of device 20 includes a cartridge 50 that fits within a complementarily-sized, tubular section 52 of cartridge retainer 32. Cartridge 50 is of conventional design, including a barrel 56 having an interior reservoir sealed at one end by a slidable plunger or piston 58 and sealed at the other end by a septum 60 held by a crimp ring 62. A needle assembly 64 shown mounted to an externally threaded proximal end 66 of retainer 32 pierces the septum 60 when so mounted after cap removal to provide an outlet during dispensing for the medication 67 filling the barrel reservoir, which medication is intended to be delivered by operation of device 20. The cartridge 50 can hold multiple doses of medicine, or even a single dose, depending on the design of device 20. The shown device 20 is a multiple use, fixed dose device, meaning that the device can be used to deliver the same dose on multiple occasions. The shown cartridge is merely one form of container from which the drive mechanism can force an emptying thereof, as, for example, a container that is compressed by action of the drive mechanism alternatively may be employed.

Device 20 also includes a drive member 70 and a driver 75 that are positioned within housing 25 to be movable for device operation. Drive member 70 extends within housing 25 along an axis of advancement indicated at A in FIG. 3, and fits or inserts within the barrel 56 of cartridge 50 to directly engage cartridge piston 58 for advancement. Driver 75 is acted upon by the drive mechanism plunger and can transfer a force to drive member 70 for advancement as further described below. Driver 75 directly engages drive member 70 and is constrained by interior surfaces of housing 25 to be axially translatable and rotatably fixed therein.

Housing piece 30 is further shown in FIGS. 6a-6f. As housing piece 30 is structurally identical to, and interacts with the remainder of device 20 in the same way as-housing piece 28, the following description of housing piece 30 will be appreciated as applying equally to housing piece 28, and further the reference numerals associated with corresponding aspects of the pieces 28 and 30 will be identical, but with a prime added to the numerals of piece 28.

Housing piece 30 is molded as a single piece of acrylonitrile butadiene styrene and includes a concave outer shell portion 80 that has its interior concavity transversely spanned by a top plate 82 and a bottom plate 84. Two curved projecting flanges 86 for securement of retainer 32 project upward from top plate 82. A semi-circular notch 88 formed in plate 82 is sized to fit the cartridge barrel 56. A notch 96 formed in bottom plate 84 provides a guided passage therethrough for plunger arms 45 and 45'.

Ribs with curved faces 90 formed on the inner surface 91 of housing piece 30, as well as an axially extending, spanning rib 92, are shaped to further support the periphery of cartridge barrel 56. A flange 94 with a stepped-down section 95 transversely extends between shell portion edges 87, 89. The transitioning region 98 of rib 92 to flange section 95, and the transitioning regions 99 from flange 94 to flange section 95, serve as contact points with the distal end of cartridge barrel 56. A semi-circular notch 125 formed in flange section 95 is concentric with notch 88 but has a smaller diameter. An inwardly directed key or finger 128 juts within notch 125 and extends distally of flange section 95.

Housing pieces 28 and 30 are designed to have select facing portions be flush together when the housing pieces are mated during assembly. In the shown embodiment, the opposite inward edges 87, 89 of shell portion 80, the inward edge 100 of top plate 82, the inward edge 102 of bottom plate 84, the inward edge 104 of each of two angled flanges 103, the inward edges 105 and 106 of flanges 94 and 95, and the inward edges 110 of a series of transversely extending, ramp-backing ribs 112 near both edges 87 and 89, are disposed along a common plane and abut their corresponding regions of housing piece 28 when pieces 30 and 28 are assembled together.

Housing piece 30 includes resilient latching prongs 115, 116 and 117, and a latching detent 119 formed on a distal extension 176 of ramp 170. Prongs 115-117 and detent 119 snap fit with related features on housing piece 28 for a fixed mating or securement of housing piece 30 with housing piece 28.

An anti-back-up pawl, generally designated 130, is disposed distally of flange section 95. Pawl 130 has an upper tip 132 designed to engage the driver member 70 described below to prevent distal drive member movement, and the pawl 130 is sufficiently resilient to allow tip 132 to splay outward during drive member advancement.

Housing piece 30 includes a pair of spaced ribs 142 and 146 that longitudinally extend along the shell interior. Ribs 142 and 146 project farther inward from shell interior surface 91 than a series of transversely extending ribs 150 that provide rigidity to the housing. The space between ribs 142 and 146 forms a driver guide channel 155.

Housing piece 30 further includes a driver slide rib 160 that longitudinally extends parallel to rib 142, and a plunger slide rib 162 that branches off from rib 160 at an angle. Ribs 160 and 162 project inward from interior surface beyond ribs 150.

On the opposite side of guide channel 155 from rib 160, housing piece 30 includes a first angled rib 165 and a second angled rib 167 parallel to each other. Rib 165 projects farther from inner surface 91 than rib 167. Rib 165 provides a support along which plunger arm 45 can slide. Rib 167 provides a support along which a projecting tip of axle pin 256 can slide, and prevents that projecting tip from contacting any of transversely extending ribs 150. Rib 165 overlaps the projecting tip of axle pin 256, thereby keeping the push module 250 and plunger arm 45 close to, but not necessarily in contact with, ramp surface 180. At the distal end of rib 165 is provided a stop rib 163, which similarly engages a projecting tip of axle pin 256, providing a distal travel stop for plunger arm 45.

A ramp, generally designated 170, projects from surface 91 beyond that of shell edges 87, 89 so as to extend into the interior of housing piece 28 when housing pieces 28, 30 are assembled together. A notch 93 in edge 87 is adapted to accommodate the lateral outward extreme region of corresponding ramp 170' of housing piece 28. Ramp 170 is fixed to housing 30 by virtue of its integral construction, but could serve its drive mechanism purpose if it were fixed to the housing by being separately made and attached so as to be axially stationary within the housing at least during dispensing. Ramp 170 includes a drive portion 172, a rounded portion 174 at the proximal end of drive portion 172, a proximal stop surface 175, a distal extension 176 and a proximal extension 178. The ramp surface 180 of drive portion 172 generally faces toward the center of the housing piece 30 or inward toward axis of advancement A. Ramp surface 180 is tilted or angled relative to the axis of advancement A. In the shown embodiment, this angling is constant along the operational length of drive portion 172 along which the plunger push module travels during injection. In an alternate embodiment, different sections of the ramp surface along its length could have different or no angling if, for example, changes to the relationship of plunger and drive member motion were acceptable or desirable, such as if the mechanical advantage provided were different or non-existent at different times of plunger motion.

Drive member 70 is further shown in FIGS. 7a-7c and is molded in one piece out of glass-fiber reinforced polycarbonate or similar material. Drive member 70 includes a foot 190 located at the top or proximal end of a longitudinally extending, rod-shaped body 192. Foot 190 serves as a load distributing element on the cartridge piston 58 that it directly engages. An enlarged end plate 194 is formed on the distal end of body 192 and is used in preventing dose setting when the medication contents of device 20 are effectively exhausted. Drive member 70 has a symmetry that allows the drive member 70 to be installed in either of two rotational orientations relative to its axis to make manufacturing assembly less complicated.

The front and back of drive member body 192 are each contoured to provide a guide channel 196 that extends the length of body 192 between foot 190 and end plate 194. One channel 196 receives a key 128 of housing piece 30, and the other channel 196 receives the corresponding key of housing piece 28, and this key and channel connection results in drive member 70 being rotationally fixed and longitudinally movable within housing 25.

The two identical, opposite sides of drive member body 192 between guide channels 196 are each referenced at 198 and include a series of one-way ratchet teeth generally designated 200. Ratchet teeth 200 are axially spaced along the length of body 192, with the distance between the corresponding portions of adjacent teeth being equal to the distance the drive member 70 is advanced to dispense a single dose from device 20. Five equally axially spaced teeth 200 are shown provided on each side 198 to achieve a device suited to deliver four identical doses, but different numbers of teeth may be used, and further the teeth need not be the same on each side of the drive member 70 if other aspects of the device or its operation were altered in alternate embodiments.

Each tooth 200 includes a ramping proximal face 202 and a distal face 204. When a distal face 204 of a given tooth is engaged by tip 132 of housing pawl 130, distal movement of the drive member 70 relative to housing 25 is prevented. When drive member 70 is then driven proximally during dose dispensing, proximal face 202 of the distally adjacent next tooth 200 serves to cam pawl 130 away from side 198 as that tooth 200 slides under pawl tip 132 until pawl tip 132 can snap into a position immediately distally of the face 204 of that tooth to be engagable with face 204.

Drive member teeth 200 are also directly acted upon by pawls of a driver 75 that is part of the mechanism that advances drive member 70.

Driver 75 is further shown in FIGS. 8a-8h and is molded in one piece out of polycarbonate or a polybutylene terephthalate/polycarbonate blend. Driver 75 has a rotational symmetry about its axis, which axis aligns with the axis of advancement A of device 20 when assembled, to facilitate assembly. Due to this symmetry, it will be appreciated that the description below of primarily the front and right half of driver 75, and its interaction with other portions of the device 20, will be recognized as having equal applicability to the rear and left half of driver 75 and its interactions with related device portions.

Driver 75 includes a main body 210 having a central hollow or bore 212 extending therethrough in which drive member 70 extends and is movable. At the proximal end of the body 210, a contoured lip 214 projects into bore 212 for engagement of end plate 194. Body 210 includes a plate portion 216 from which a longitudinally extending rib 218 projects. Plate portion 216 is slidably supported by the ribs 142' and 146' of housing piece 28 shown in FIG. 5, and rib 218 fits within the driver guide channel 155' of housing piece 28. The driver 75 is further supported within the housing 25 by a transversely extending bar portion 220 of body 210 that slides along a driver slide rib 160' of housing piece 28.

A flexible finger or pawl 224 of driver 75 projects from the proximal end of main body 210 at an angle toward the axis of advancement A of device 20. The tip 225 of pawl 224 is adapted to engage distal faces 204 of the teeth 200 at select times to allow for a driving advancement of drive member 70 for dispensing doses. Pawl 224 is flexible so that tip 225 can slide along proximal face 202 and over the crest of tooth 200 to snap behind distal face 204. Pawl tip 225 is sized and positioned to engage only a portion of the transverse height of a given tooth 200 so that pawl 224 and pawl 130 can each effectively engage the same tooth 200 simultaneously at the end of a dispensing.

A pair of identical ramp elements 240 of driver 75 project laterally from main body 210 with a space or gap 244 therebetween. The pair of elements 240 is provided in the shown embodiment to work with the push module 250 shown, but a pair is not required in other embodiments. Ramp elements 240 include a ramp surface 242 that faces away from the center of the housing piece 30 and that is tilted or angled relative to the axis of advancement A. The angling is shown as being constant along the axial length of ramp elements 240, but could also be different depending on the configuration of the ramp surface 180 and intended operation of device 20. The angling of ramp surface 242 from the axis of advancement A is greater that angling of the ramp surface 180 such that the planes in which ramp surfaces 180, 242 are disposed converge as they extend proximally. The specific angling of the ramp element 240 relative to the axis of advancement A is selected to result in a proper travel distance for driver 75 during a dispensing operation as described further below. Changing the angling of the pair of ramp elements 240 with respect to the axis of advancement A, with no changes to ramp surface 180, can achieve different driver motions. For example, a drive member 70 with five sets of teeth 200 is highly suitable for use to dispense four doses, but if six sets of teeth for dispensing five smaller-volume doses was used than a smaller angling of the ramp elements 240 would be employed, while for four sets of teeth for three larger-volume dose dispensings a larger angling of the ramp elements 240 would be employed. When the angling of ramp elements 240 is changed, their proximal end stays in the same relative position and their distal end therefore moves, either proximally (for a larger angling) or distally (for a smaller angling). As the angle of ramp elements 240 is so changed, the overall lengths of other driver portions, such as plate portion 216 and rib 218, and the relative position of hook member 230, all also change so as to maintain the general design illustrated in FIGS. 8a-8h and all functions described herein.

Driver 75 also includes a hook member 230 that juts laterally from the distal end of plate portion 216. Hook member 230 is used in the setting of driver 75 to prepare for a dispensing operation.

With reference again to FIGS. 1-5, the shown plunger is formed by button 40, plunger arms 45 and 45', and push modules, generally designated 250 and 250', disposed on the proximal ends of plunger arms 45 and 45' respectively. It will be appreciated that the plunger can be differently configured, such as if the converging ramp feature of the drive mechanism were only provided on one side of drive member 70 instead of the two sides as shown, in which case the plunger arm 45' and its push module 250' could be eliminated.

Figure 5:
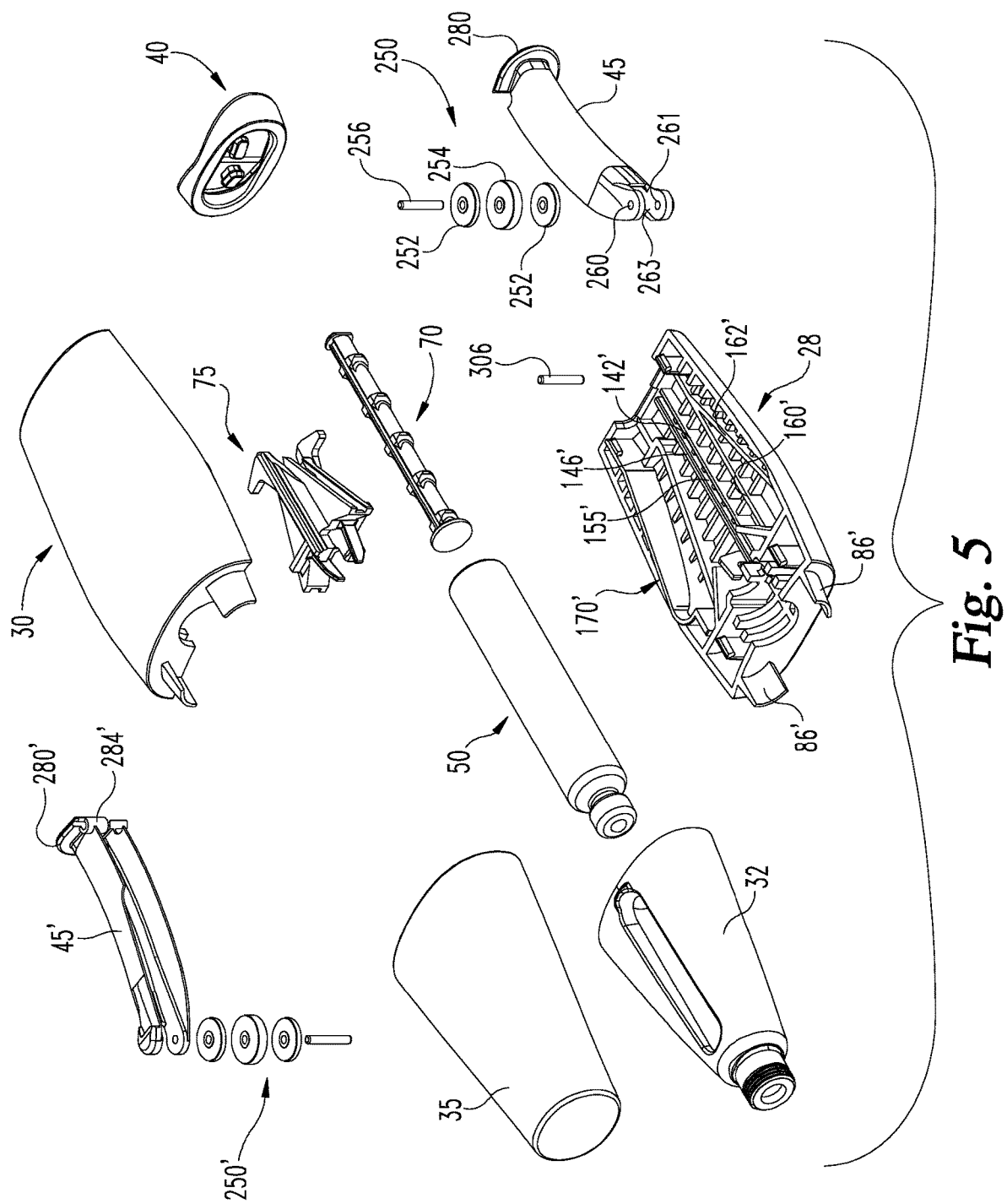
FIG. 5 is an exploded perspective view of the device of FIG. 1.

The push modules 250 and 250' are shown in exploded form in FIG. 5 and serve similar purposes, so that the following description of push module 250 generally applies to push module 250' as well. Push module 250 includes two identical rollers or wheels 252 that flank opposite sides of a single roller or wheel 254. Wheels 252 and wheel 254 are each formed of a stiff, lubricious plastic so as to roll along the different ramp surfaces they respectively engage. Wheels 252 have a smaller diameter than that of wheel 254 so as to insure that wheel 254, and not wheels 252, contacts ramp surface 180. This allows wheel 254 to roll along ramp surface 180, while wheels 252 which rotate in the opposite direction (along ramp surface 242) do not drag along ramp surface 180. Wheels 252 and wheel 254 are rotatably disposed within the gap 263 between plunger tips 262 and 264 and are concentrically arranged and journaled to an axle pin 256 that fits through hole 260 and within blind bore 261 formed in plunger tips 262 and 264, respectively. Wheels 252 rotate about axle pin 256 during use in the opposite direction that wheel 254 rotates.

Each wheel 252 is for rolling engagement with a different ramp surface 242, and wheel 254 is for rolling engagement with ramp surface 180. The use of two wheels 252 for push module 250, and the use of two corresponding ramp surfaces 242, is for balancing forces on pin 256 and driver 75, but such is not required. Still further, all or part of the push module need not roll along the ramp surface(s). In an alternate embodiment, and although some frictional resistance may be added, one or more of the rotating wheels could be replaced with a non-rotating block or glide wedge, possibly made of a low friction material such as PTFE (Teflon) or silicone-oil-impregnated thermoplastic, that slides along the ramp surface it engages. Still further, the wheels 252 and 254 could be made together as a monolithic, non-rotating block or glide.

Plunger arm 45, which is structured identical to and functions similarly to plunger arm 45', is further shown in FIGS. 9a-9j and is molded in one piece out of polycarbonate or acrylonitrile butadiene styrene. Plunger arm 45 includes an end plate 280 with a notch 282. A pin-receiving sleeve 284 is formed on the underside of end plate 280. A U-shaped channel body 286 projects upward from plate 280 in a curved shaped and transitions to two facing leg portions 292, 294. The U-shaped channel permits plunger arms 45 and 45' to surround drive member 70 without contact or interference when the plunger is in the fully proximal position. The curvature of body 286 is arranged such that as the plunger is moved distally and proximally in device use (during which motion it both translates and rotates) the gap between body 286 and housing notch 96 remains small and constant. Furthermore, the edges 304 of plunger arms 45 and 45' are made to overlap during the full range of travel. Together these prevent the opening of large gaps into the interior of housing 30, affording protection from the unwanted entry of debris. The cut out 305 of edge 304 below leg 292 provides clearance with ramp surface 242 when the plunger is its proximal position. Leg portions 292, 294 are spaced to define gap 263 and respectively have upper ends or tips 262, 264.

The forward face of tip 264 includes a projecting boss 298 having a forward facing glide surface 300 and a distal edge 302. Glide surface 300 is backed by and slides along slide rib 162' of housing piece 28. Boss edge 302 is used to engage hook member 230 during dose preparing.

Plunger arms 45 and 45' are connected together to allow a limited movement relative to each other that occurs during device use. The connection in the shown embodiment is a pivotal connection accomplished with a pin 306 that fits within sleeve 284 and 284' of plunger arms 45 and 45' respectively.

Figure 10B:
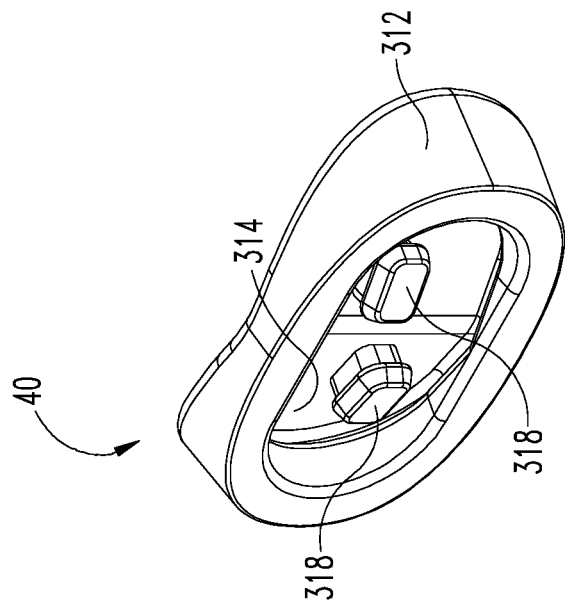
FIGS. 10a and 10b are bottom and top perspective views, respectively, of a plunger button of the device of FIG. 1.
Figure 10A:
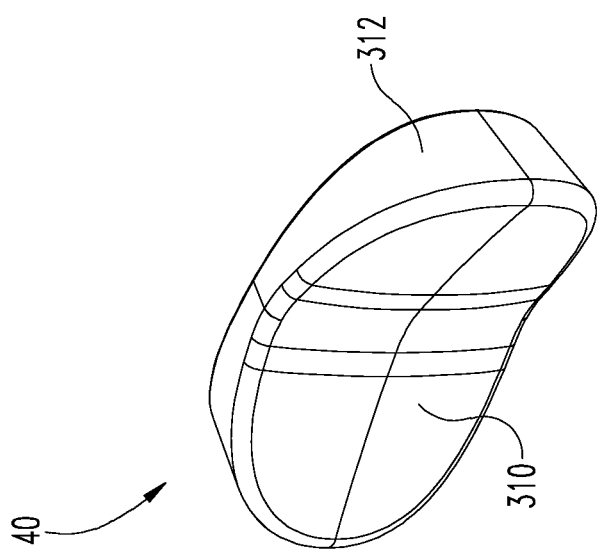

Plunger button 40 is further shown in FIGS. 10a and 10b and is molded in one piece out of a resilient material such as liquid silicone rubber or thermoplastic elastomer. Button 40 includes a contoured push surface 310 and a ringing periphery 312. Button periphery 312 is grippable by a user for plunger withdrawal during dose setting, and push surface 310 is directly pressable by a user for plunger plunging during dose dispensing. A cavity 314 in the proximal face of button 40 receives end plates 280, 280' during device assembly, and button 40 is fixedly secured to the plunger arms 45, 45' by the interfitting of two prongs 318 into notch 282 of arm 45 and the corresponding notch of arm 45'.

The structure of the drive mechanism of dispensing device 20 will be further understood in view of the following description of its operation. The following description is provided as to the right side of the drive mechanism shown in FIGS. 11-16, and it will be appreciated that the left side of the drive mechanism operates identically thereto.

Initially, device 20 will be provided as shown in FIG. 1. To prepare the device for the delivery process, a user first removes cap 35, and installs a needle assembly 64, resulting in device 20 being arranged essentially as shown in FIG. 4. The device plunger is then operated in a pull and then plunge fashion relative to the housing 25 to cause device 20 to dispense a dose through the needle assembly 64 and into an injection site where the needle of the assembly 64 was inserted for the dose dispensing.

Figure 12:
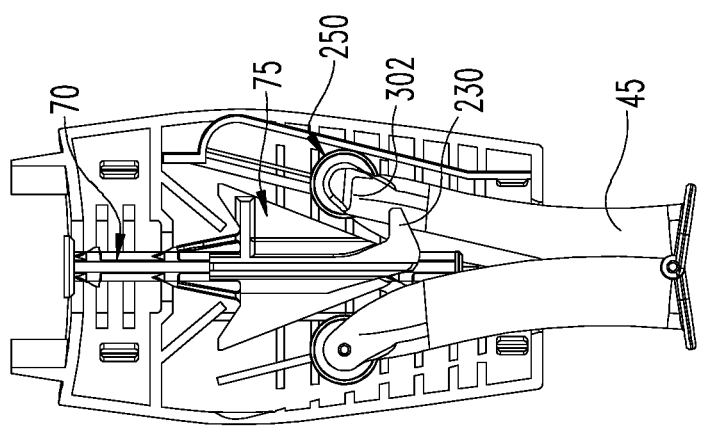
FIG. 12 is a front view similar to FIG. 11 while in the process of being shifted to set the second dose for delivery.

This pull and then plunge operation of the device plunger is explained with reference to FIGS. 11-16, which shows pertinent parts of the device 20. It will be appreciated that the arrangement of the device components shown in FIG. 11 corresponds to the device arrangement after a first dose has already been injected. The plunger is arranged in a ready-to-set axial position. To prepare a dose for injection, the user grips the periphery of the button that is not shown in FIG. 11 but which is covers flanges 280, 280' of the plunger and pulls the button downward relative to the device housing. Initially as the plunger button is so pulled downward, the plunger moves proximally independently of the driver 75. FIG. 12 shows the arrangement of the parts of FIG. 11 at a mid-point of the plunger being pulled downward in a dose preparing or setting stroke.

Figure 13:
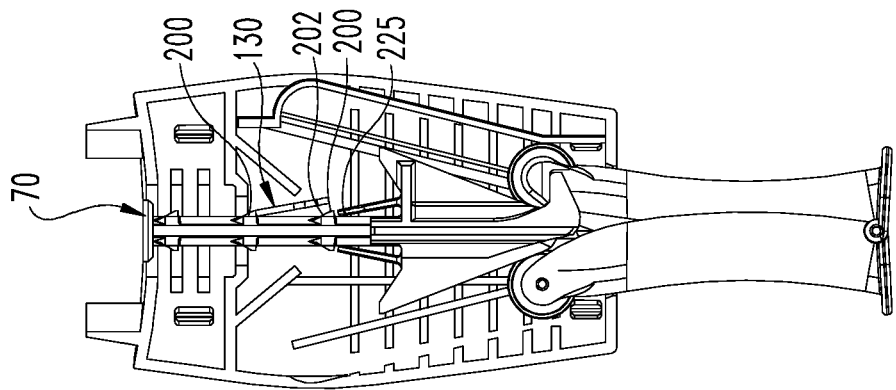
FIG. 13 is a front view similar to FIG. 12 after having been set to deliver the second dose.
Figure 11:
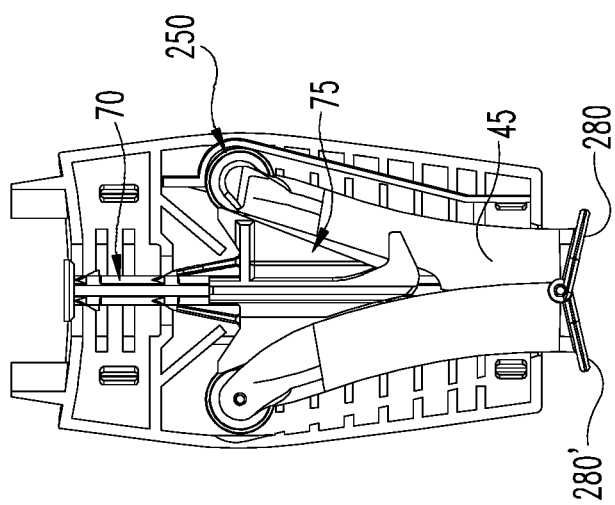
FIG. 11 is a front view of a portion of the device of FIG. 4 after having been operated so as to have delivered a first dose.

As the plunger is shifted proximally, the boss distal edge 302 is pulled into abutting contact with hook member 230, and as the plunger is continued to be pulled downward, the driver 75 is also pulled downward at the same speed and the same amount as the plunger. During this movement, drive member 70 is not moved distally due to the pawl 130 engaging a distal face 204 of a tooth 200. As driver 75 is pulled downward, its tip portion 225 slides along drive member side 198 until it reaches tooth proximal face 202, at which time face 202 serves to cam tip 225 outward such that the tip 225 passes over tooth 200 and snaps inward distally of distal face 204 of the tooth that is directly distal of the tooth engaged by pawl 130. Should the user not pull the plunger distally all the way out, tip 225 will not snap over tooth 200, resulting in no click and no resistance to moving the plunger proximally. This will be evident to the user. These audible and tactile cues together remind the user to follow the correct steps of use. As the plunger is pulled distally, it reaches an end of travel when a projecting tip of axle pin 256 engages stop rib 163. At this point, the device components of FIG. 11 are now arranged as shown in FIG. 13, at which the plunger, as well as the driver 75, are in ready-to-inject axial positions and the device is ready for an injection.

The user is then able to operate device 20 to dispense the set or fixed dose by pressing the plunger button to drive the plunger back toward the housing. This movement forces the plunger arm 45 to move upward and after any mechanical backlash resulting from manufacturing tolerances is crossed, wheels 252 are in rolling engagement with driver ramp surfaces 242 and wheel 254 is in rolling engagement with housing ramp surface 180. The location of the ramp surfaces 242 and 180 and the fact that in the proximal direction the ramp surfaces 242 and 180 converge results in these surfaces immediately proximate of push module 250 being sized and positioned to prevent the push module 250 from continuing to move upward until the driver is moved upward or proximally within the housing.

Figure 15:
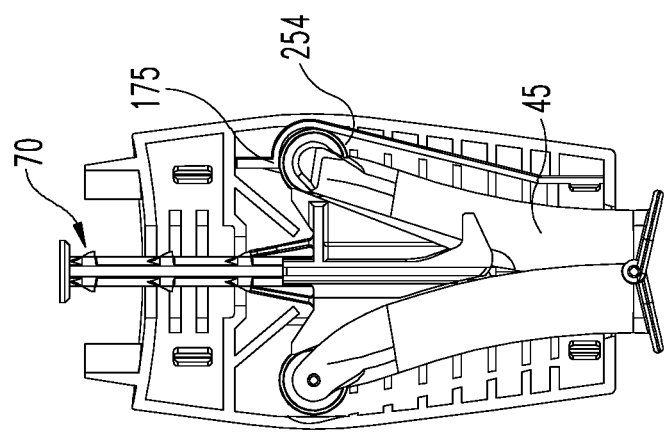
FIG. 15 is a front view similar to FIG. 14 after having been operated so as to have delivered the second dose.
Figure 14:
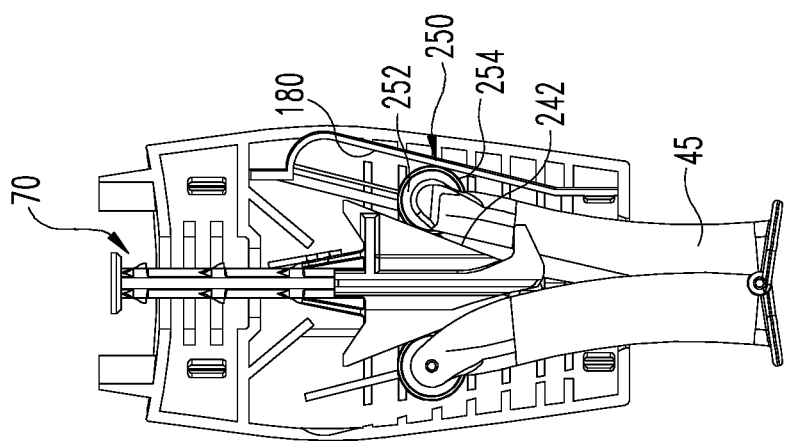
FIG. 14 is a front view similar to FIG. 13 while in the process of being shifted to deliver the second dose.
Figure 17:
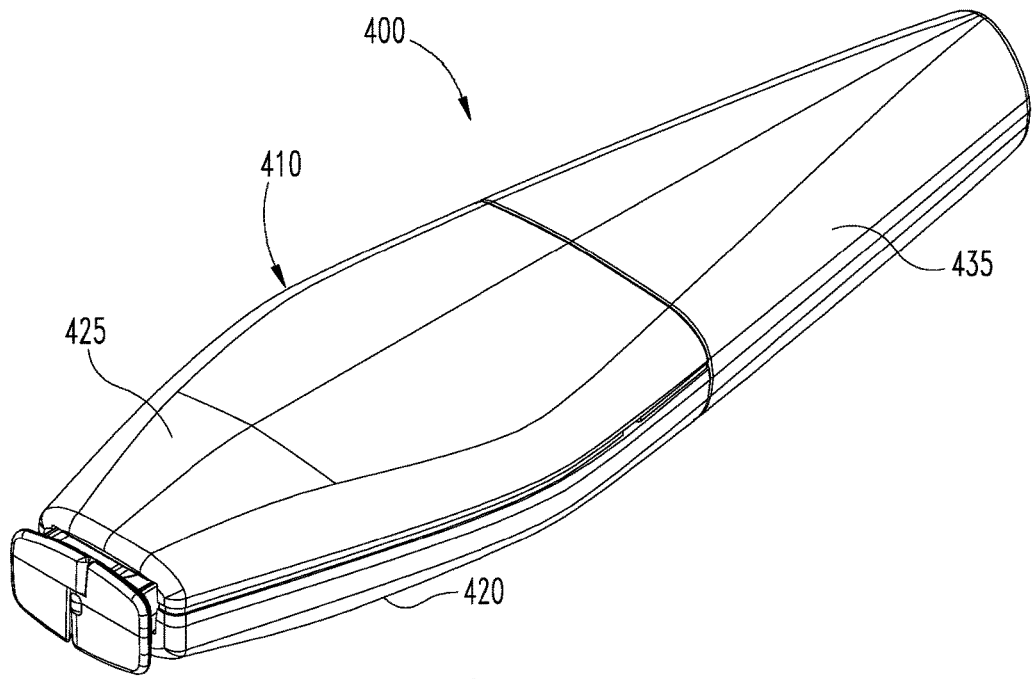
FIG. 17 is a perspective view of a second embodiment of a medication dispensing device that is equipped with a mechanical-advantage-providing drive mechanism that utilizes converging ramps.
Figure 18:
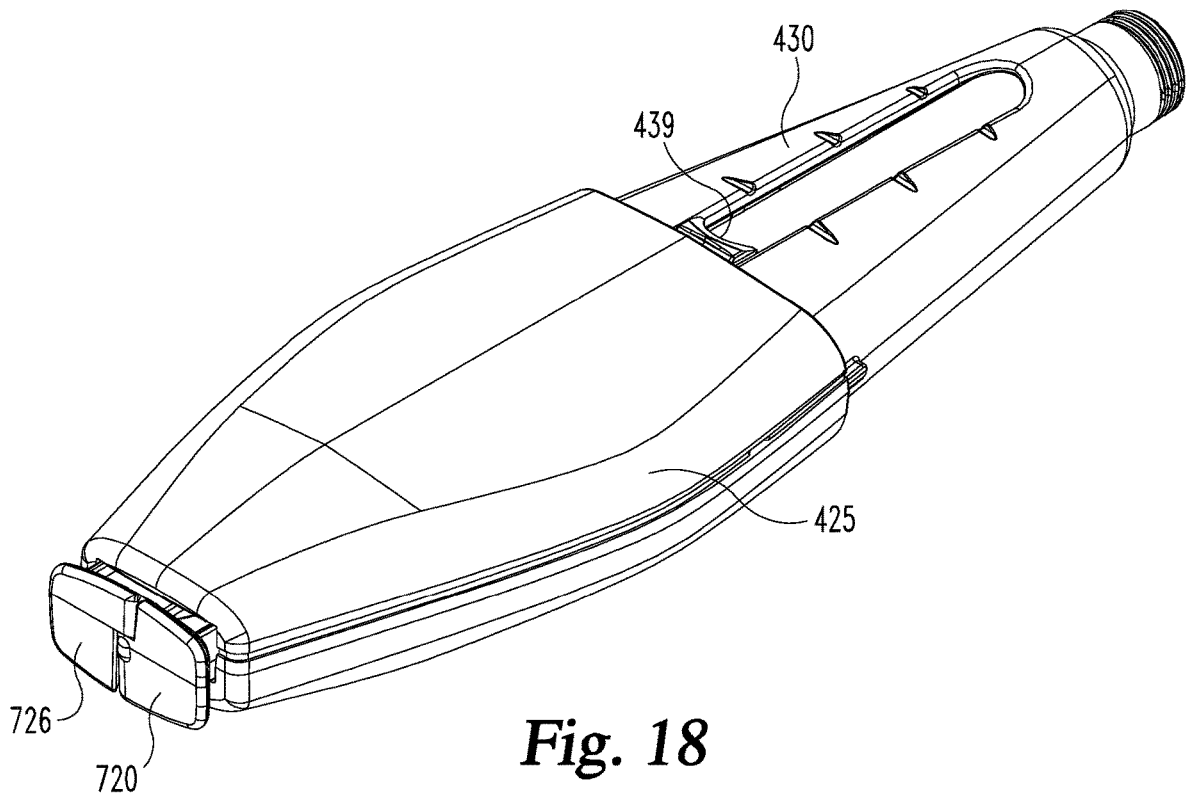
FIG. 18 is a perspective view of the medication dispensing device of FIG. 17 after the cap has been taken away.

Such upward driver movement is forced by the push module 250 acting on the ramp surfaces 242 and 180 as the plunger is driven upward. The driver 70 moves fractionally upward of what the plunger moves upward during this movement. As the driver 75 is moved upward, due to the engagement of its pawl tip 225 with tooth 200, the drive member 70 is also advanced, which forces cartridge piston 58 farther into the cartridge barrel 56 to force medicine 67 through the needle assembly 64. As the upward plunger movement continues, the push module 250 continues to encounter a lateral gap between the ramp surfaces 242 and 180 which is too small to allow passage of the push module 250 unless the driver 75 continues to move proximally. FIG. 14 illustrates the device components at an intermediate phase of the plunger upward advancement. While a user could stop injecting at an intermediate point, they are instructed to not do so, and will be unable to prepare device 20 for a subsequent dose prior to completing the current dose. The plunger movement and the resulting movement of the driver 70 continues until wheel 254 abuts proximal stop surface 175 so that further plunger and driver advancement is halted. Shortly before the plunger reaches this position within tolerances, the drive member 70 has been advanced sufficiently proximally to dispense the set dose from cartridge 50 and such that the tooth 200 engaged by pawl tip 225 has passed housing pawl 130 such that housing pawl tip 132 has snapped behind the distal face 204 of that tooth to prevent drive member retraction. FIG. 15 illustrates the device components at this phase of operation.

Figure 16:
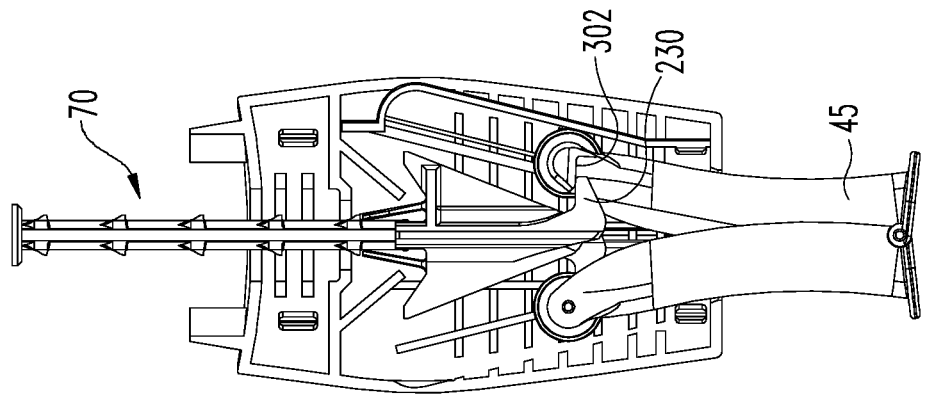
FIG. 16 is a front view similar to FIG. 15 after the last dose has been delivered and the plunger retraction that would have been necessary to set another dose if available has been halted.

The device can be continued to be used until the contents of the cartridge are dispensed as individual doses. When the cartridge no longer has a dose to be dispensed, the device 20 prevents a user from setting or cocking the device for an additional dose. In particular, when the user attempts to pull the plunger distally and the boss distal edge 302 abuts hook member 230 the driver begins to move rearward. However, when the driver lip 214 abuts end plate 194 of drive member 70, the driver 75 can no longer move distally within the housing 25. Due to its engagement to hook member 230, the plunger similarly is prevented from moving further distally relative to the housing. The device components of FIG. 16 illustrate this configuration that indicates to a user that the device is no longer suitable for dispensing.

Referring now to FIGS. 17-21, there are shown various view of another device, generally designated 400, equipped with a drive mechanism that uses converging ramp surfaces. It will be appreciated by one of skill in the art that dispensing device 400 is conceptually similar to device 20 in many respects that are not all expressly listed below, and device 400 further includes certain modifications identified below that, among other things, facilitate device construction or ease of use, including via an increased mechanical efficiency.

The protective housing 410 of dispensing device 400 includes a housing back piece 420, a housing front piece or lid 425, and a cartridge retainer 430. Cartridge retainer 430 snap fits during device manufacture to the assembly of housing back piece 420 and housing lid 425. A removable cap 435 fits over cartridge retainer 430 and is releaseably secured to the housing 410 via its engagement with detents 437 and 439 respectively provided on housing back piece 420 and lid 425.

The plunger of device 400 includes two plunger arms 442 and 444 that extend from the interior of housing 410 and which include distal end plates 720 and 726 that form a plunger button or user pushable element. Each of plunger arms 442 and 444 are equipped with push modules used to engage ramps and advance driver 450.

Driver 450 is acted upon by the drive mechanism plunger and advances drive member 455. Driver 450 directly engages drive member 455 and is constrained to be axially translatable and rotatably fixed within the housing. Drive member 455 extends along an axis of advancement and fits within barrel 462 of cartridge 460 to advance cartridge piston 464. Cartridge 460 is identical to cartridge 50 and includes a septum 466 pierceable by an injection needle assembly 470 mountable to cartridge retainer 430.

The housing back piece 420 and housing lid 425 which when assembled form the distal portion of housing 410 are further shown in FIGS. 24a-f and FIGS. 25a-f. Back piece 420 includes an outer shell portion 480 that has an interior concavity 482. A bottom plate portion 484 spans the distal end of outer shell portion 480 and includes a notch 486 with lobes 488 for accommodating the plunger. Two axially extending flanges 492 formed on the interior of shell portion 480 project upward beyond the proximal end 490 of shell portion 480. Flanges 492 are spaced laterally, or in the transverse direction, and include at their proximal ends inwardly facing latch features 494 that extend forward beyond the rest of flanges 492.

Assembly rails 500 are formed along a distal region of each side edge 498 of shell portion 480, and project forward beyond the rim surface 502 of shell portion 480. Rails 500 are angled in transverse cross-section and arranged to define outwardly projecting lips 503.

Housing lid 425 includes an outer shell portion 510 that has an interior concavity 512 that is shallower than shell concavity 482. A bottom plate portion 514 spans the distal end of outer shell portion 510 and includes a notch 516 for the plunger. Two axially extending flanges 520 formed on the interior of shell portion 510 project upward beyond the proximal end 521 of shell portion 510. Flanges 520 also project rearward beyond the rim surface 522 so as to abut flanges 492 when housing 410 is assembled. Flanges 520 include at their proximal ends outwardly facing latch features 524 that engage the forwardly extending latch features 494 when flanges 520 and 492 abut each other. Flanges 520 are spaced laterally so as to accommodate cartridge 460.

Along a distal region of each side edge 526 of shell portion 510, an undercut area 528 of the shell interior is formed for housing assembly purpose. During manufacturing assembly, after appropriate internal parts of the device have been installed into housing back piece 420, the housing lid 425 is moved into a mating configuration with back piece 420, with rim surface 522 contacting rim surface 502, but with housing lid 425 being offset in the axial direction from back piece 420 to be slightly distally thereof. In such a configuration, rails 500 and lips 503 fit within interior concavity 512 but do not extend laterally into undercut areas 528. When so aligned, as a subsequent step of assembly, housing lid 425 is slid proximally relative to back piece 420. This sliding movement causes lips 503 of rails 500 to slide into undercut areas 528, and latch features 494 to slide into latching engagement with latch features 524, effectively securing the housing lid 425 and back piece 420 together in the state shown in FIG. 17. When cartridge retainer 430 is subsequently assembled to the latched subassembly of housing back piece 420 and housing lid 425 by retainer legs 530 fitting into the subassembly so that latch elements 532 snap fit under housing ribs 534, the engaged latch features 494 and 524 are further constrained by the cartridge retainer ribs 536 that prevent lateral movement of the flanges 492 and 520, and by the cartridge retainer interior surface 538 that limits forward and rearward movement of the flanges 492 and 520.

On back piece 420 and housing lid 425, the interior surfaces of flanges 540 and 542 are shaped to support the periphery of cartridge barrel 462, and pairs of stepped ribs 544, 546, 548 and 550 engage the distal end of cartridge barrel 462. An inwardly directed key 555 juts above cross rib 557.

A pair of anti-back-up pawls, generally designated 560, project forwardly or inwardly from shell interior surface 562 distally of cross rib 557. Each pawl 560 has a proximal tip 564 that prevents distal movement of drive member 455 but which allows drive member advancement.

Housing back piece 420 includes a series of axially spaced, transversely arranged ribs 568 and a pair of longitudinally extending ribs 570 that project inward farther than ribs 568. Ribs 568 provide supports on which can slide drive member 455, and ribs 570 aid in keeping drive member 455 axially aligned.

Housing back piece 420 also includes a pair of support ribs 575 that longitudinally extend and along which slides driver 450. Laterally offset and extending at an angle from ribs 575 are a pair of backing ribs 578. A second set of angled ribs 580 run parallel to ribs 578 at positions laterally outward thereof and ribs 580 do not project from the shell interior as far as ribs 578. Ribs 580 provide a support along which the rear facing surfaces of bosses 742, 774 of plunger arms 442, 444 can slide. Ribs 578 provide supports along which plunger arms 442, 444 can slide and further by engagement with the laterally inward faces of bosses 742, 774 keeps the plunger arms 442, 444 close to, but not necessarily in contact with, ramp surfaces 592. When the plunger is pulled all the way out, bosses 742, 774 hit stub walls at the proximal end of ribs 580.

A pair of ramps, generally designated 590, are disposed laterally outward of ribs 580 on housing back piece 420. Ramp surfaces 592 are disposed at a constant angling relative to the longitudinal axis of device 400 along their entire operational length.

Housing lid 425 includes an axially extending guide rib 600 that is centered along the shell transverse width and which is used to guide driver 450. Four support ribs 602 that longitudinally extend slidably support driver 450. Angled ribs 604 provide a support along which the forward facing surfaces of bosses 740, 772 of plunger arms 442, 444 can slide. Ribs 606 provides supports along which plunger arms 442, 444 can slide and further back up bosses 740, 772.

Referring now to FIG. 27a-27e, drive member 455 includes a foot 620 located at the top or proximal end of a longitudinally extending body 622 that is generally rectangular in transverse cross section. Body 622 is not centered on foot 620 as body 622, due to the stacking of parts of device 400, has it center positioned more rearward within the device thickness than is the center of foot 620 that is centered within the front-to-back thickness of device 400.

The rear face 624 of drive member body 622 includes a longitudinally extending channel 626 along its length. Channel 626 receives key 555 of housing back piece 420 so that body 622 is constrained to move longitudinally and not rotationally within housing 410. The forward face 628 of drive member body 622 similarly includes a longitudinally extending channel 629 along its length which is shallower in depth. Channel 629 interacts with driver 450 as described further below.

The opposite side faces 634 and 636 include a series of one-way ratchet teeth generally designated 640. Ratchet teeth 640 are axially spaced along the length of body 622, with the distance between the corresponding portions of adjacent teeth being equal to the distance the drive member 450 is advanced to dispense a single dose from device 400. Each tooth 640 includes a ramping proximal face 642 and a flat distal face 644 against which a force can be applied by pawls 560 and driver pawls 680 described below. Body side faces 634 and 636 each also include a test tooth 668 which is engaged by the pawls 560 and the driver pawls 680 when a device is newly assembled. Test tooth 668 allows the correctness of the assembly to be tested by the manufacturer operating the device once, before the cartridge is mounted, which results in the drive member 450 moving proximally only slightly, after which the pawls 560 and driver pawls 680 engage the distal face 644 of the most proximal tooth 640 in preparation for an initial medication delivery as done in device 20.

Driver 450 is further shown in FIGS. 28*a*-28*d* and includes a generally triangular body portion 675. A boss 677 projects from the rearward facing surface 679 of body portion 675. Boss 677 slidably fits within channel 629 of drive member body 622, and its abutment with channel wall 627, which may occur when the driver 450 is attempting to be pulled distally, prevents device 420 from being reset after its last dose has been delivered.

Two flexible pawls 680 also project at an angle from a base portion 682 projecting from rearward facing surface 679. Pawl tips 683 engage teeth faces 644 for advancement of drive member 455. Recesses shown in body portion 675 reduce material use as well as reduce sink.

The periphery of body portion 675 forms a pair of mirror image ramp surfaces 690 that are straight along their lengths Ramp surfaces 690 each terminate at their proximal end in a curved region 692 that forms a stop for the plunger glides 736, 768 in the event that a user presses the plunger with excessive force, causing the plunger arms to flex laterally and the glides to travel proximally further than the corresponding motion of driver 450 in ordinary use.

Driver 450 also includes a bar-shaped body portion 695 that is forward of forward facing surface 681 and that extends distally of body portion 675. A pair of axially extending rails 698 on body portion 695 are transversely spaced to define an axially extending channel 700. Guide rib 600 of housing lid 425 fits within channel 700 so as to guide motion of driver 450 in the axial direction.

Figure 19:
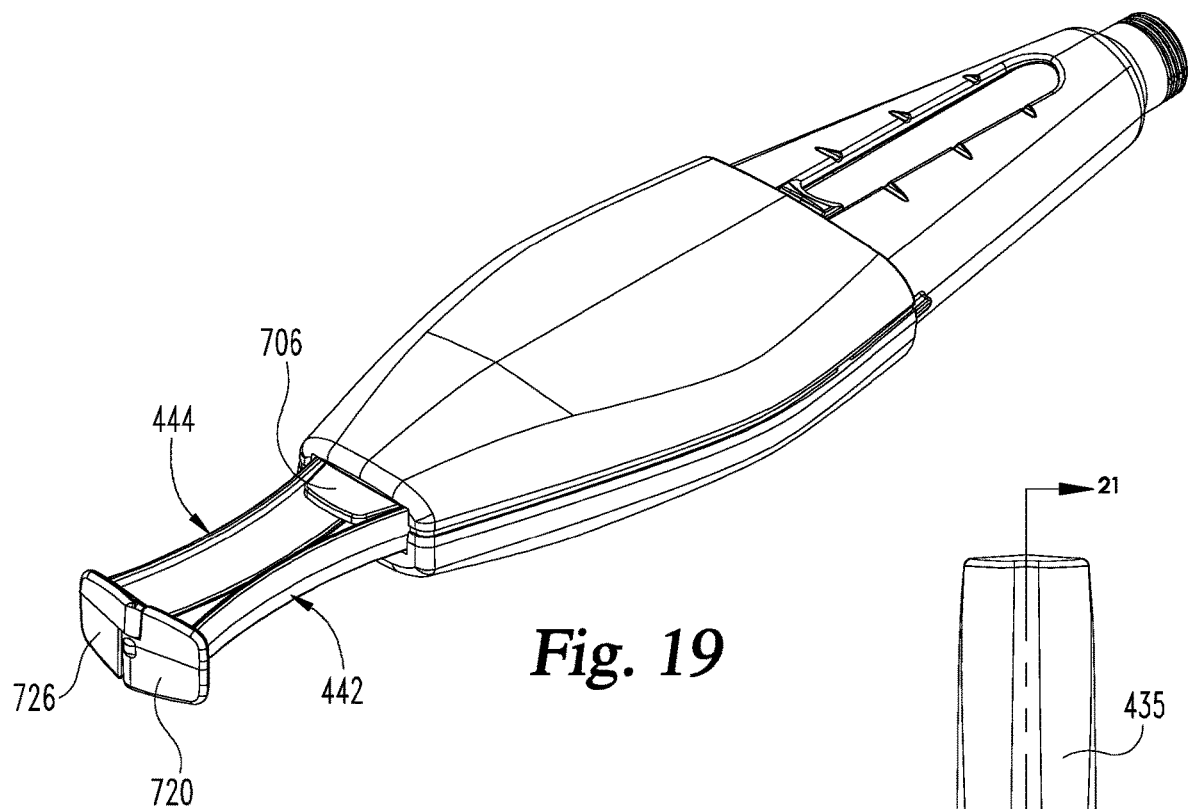
FIG. 19 is a perspective view similar to FIG. 18 after the device has been set to deliver a dose.
Figure 20:
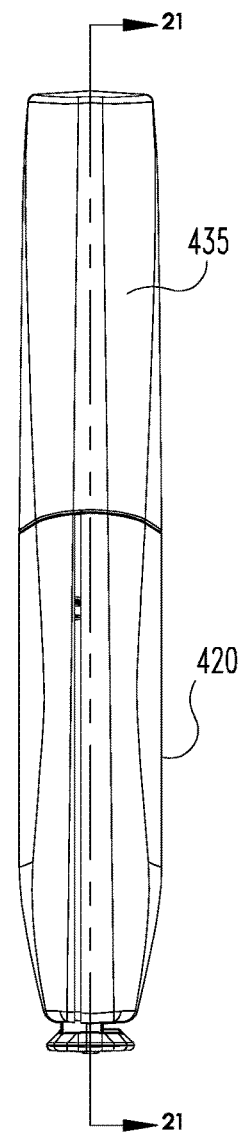
FIG. 20 is a side view of the medication dispensing device of FIG. 17.

The distal end of body portion 695 includes a transversely enlarged plate 704 having a rounded distal tip region 706 as well as proximally facing pull surfaces 708. Pull surfaces 708 allow plate 704 to serve as a driver hook for setting purposes. Tip region 706 serves as a flag element that fits through notch 516 when device 400 is properly set for a dispensing operation as shown in FIG. 19, thereby serving as a ready to use indicator. Tip region 706, whether it be by choice of materials or construction or added coloring or the like, is preferably a different color or otherwise distinguishable from the housing 410 to be readily visible by a user.

The plunger of device 400 includes two interconnected plunger arms 442, 444 that are each formed with two axially spaced push modules. The plunger arms are made from an injection molded plastic such as polyoxymethylene, also known as acetal. Plunger arm 442 is further shown in FIGS. 29*a*-29*h*, and plunger arm 444 is further shown in FIGS. 30*a*-30*h*. Plunger arm 442 includes an end plate 720 from which a flat member 722 projects in the proximal direction. A pin 724 projects forward from an edge of end plate 720 and is received in a rearward facing socket 728 formed in end plate 726, which pin and socket interaction pivotally interconnects the plunger arms 442 and 444. The distal faces of end plates 720 and 726 together provide a push surface upon which a user can apply a plunging force to the device plunger.

Plunger arm 442 includes a flange 730 on the laterally outward edge of member 722 along the majority of its length. Flange 730 extends both forward and backward of member 722 for rigidity and axially slides within a housing notch lobe 488 during plunger motion. The curvature of flange 730 is so arranged that as the plunger arm translates and rotates between its distal to proximal positions, the flange does not contact housing notch lobe 488. The forward face 732 of member 722 includes a scalloped recess 734 along its laterally inward edge that accommodates overlap with plunger arm 444 during use.

At its proximal end, member 722 includes a laterally inwardly facing, rounded tip surface or glide 736 that serves as a push module that non-rollingly engages driver ramp surface 690 as it slides therealong. The rounding of glide 736, which may have a radius of curvature of 3 millimeters, results in a small contact region with ramp surface 690 that allows force to be applied thereat but with limited frictional resistance due to the use of low friction coefficient acetal for the plunger arm.

At the proximal end of flange 730, a second glide or push module 738 is integrally provided that projects laterally outward from flange 730. Glide 738 has a rounded surface 739 having a radius of curvature of 3 millimeters and serves as a as a push module that engages housing ramp surface 592 as it slides therealong.

Unlike in device 20 in which the push modules 250 are concentric and engage the housing and driver ramps at nearly the same axial location within that device, glides or push modules 736 and 738 are not concentric and are more axially spaced such that the driver engaging push module 736 is disposed proximally of the housing engaging push module 738, which arrangement provides a higher mechanical efficiency. In operation the arrangement of surface normal forces and frictional forces is such that when push module 736 is made increasingly proximal of push module 738, the relative loss of power due to friction decreases. Since minimizing power loss is commonly seen as desirable because it lowers glide force or user effort, embodiments that increase this proximal offset are preferred. However as this offset is increased the device may increase in overall size and/or the individual components may become more complex in design and more costly to manufacture and assemble. The shown embodiment has a proximal offset while balancing the competing needs of size and relative component simplicity. With modifications the push modules may in an alternate embodiment be disposed generally concentrically as in device 20 as described above, or such that the driver engaging push module 736 is disposed distally of the housing engaging push module 738 if a lesser mechanical efficiency is desired.

Figure 21:
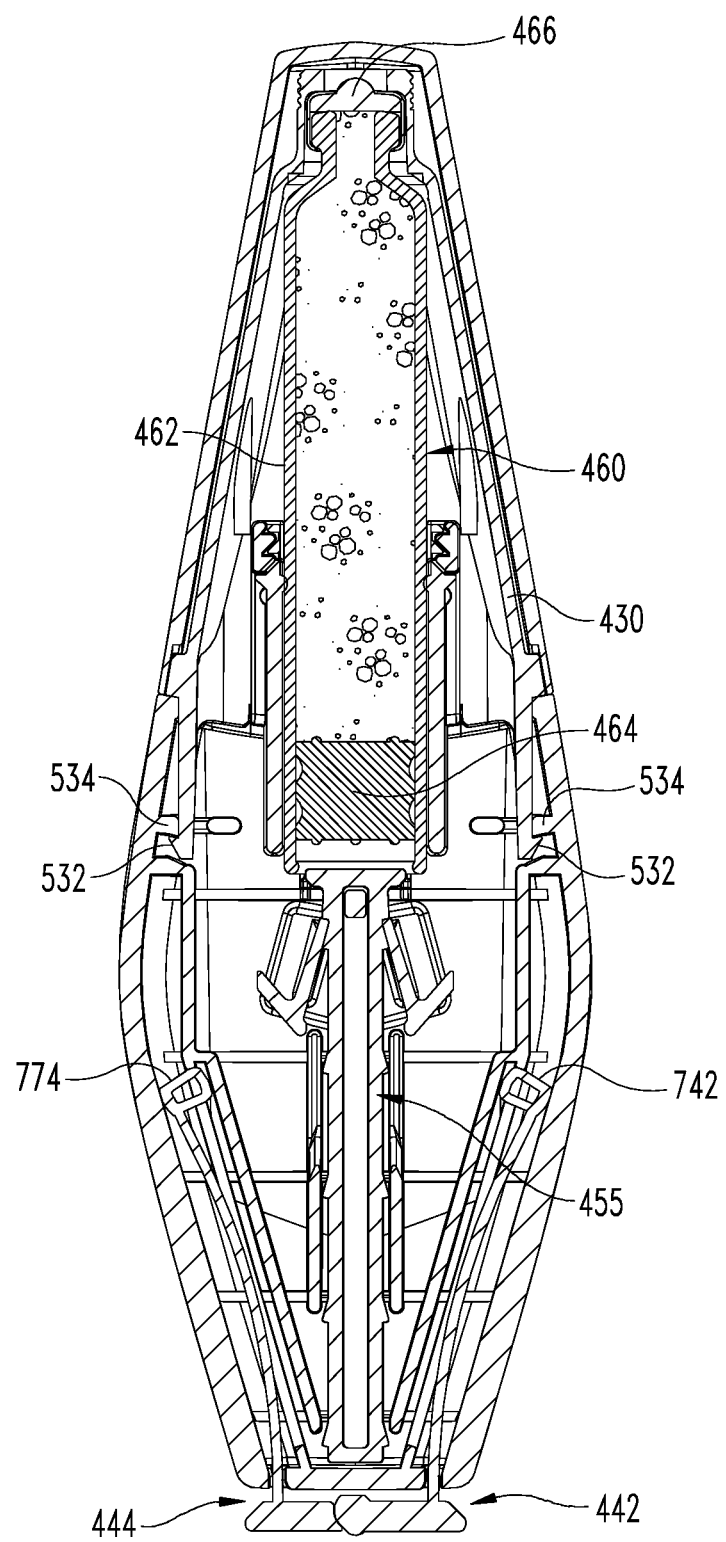
FIG. 21 is a front view in longitudinal cross-section taken along line 21-21 in FIG. 20 of the device of FIG. 17.
Figure 22:
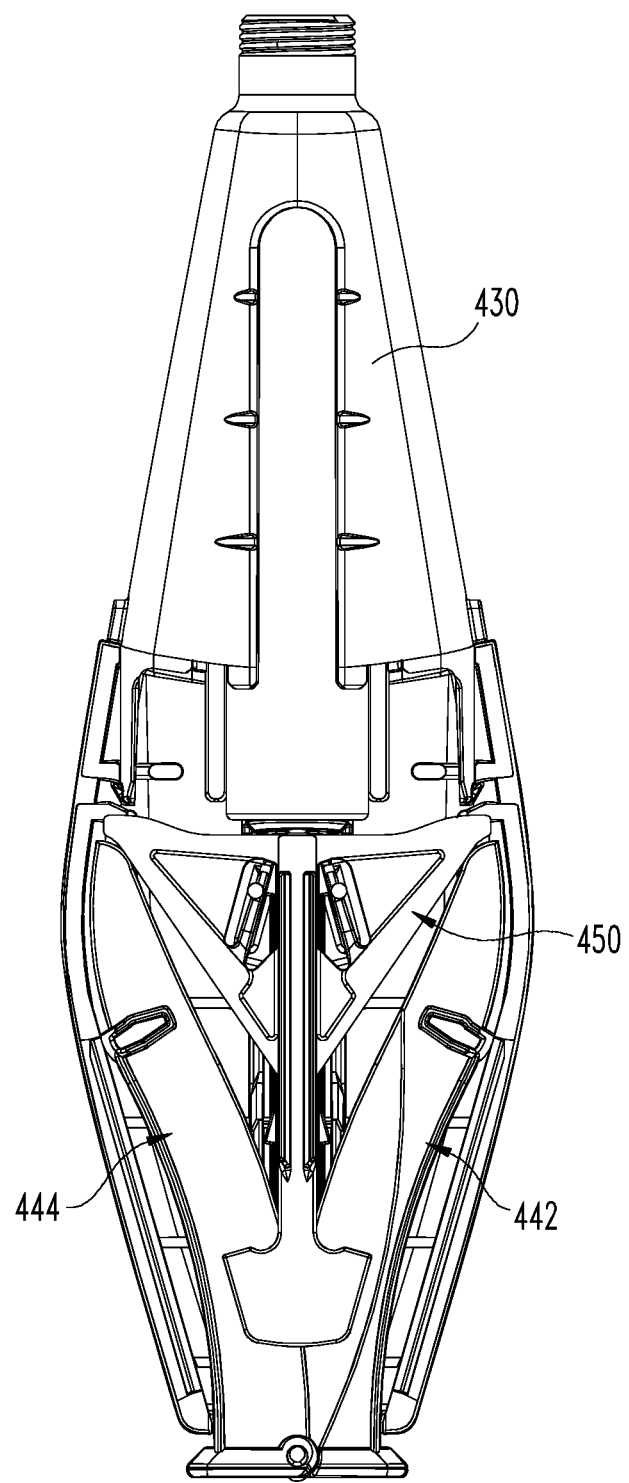
FIG. 22 is a front view of the medication dispensing device of FIG. 17 after the cap has been taken away and with a front distal housing piece removed.
Figure 23:
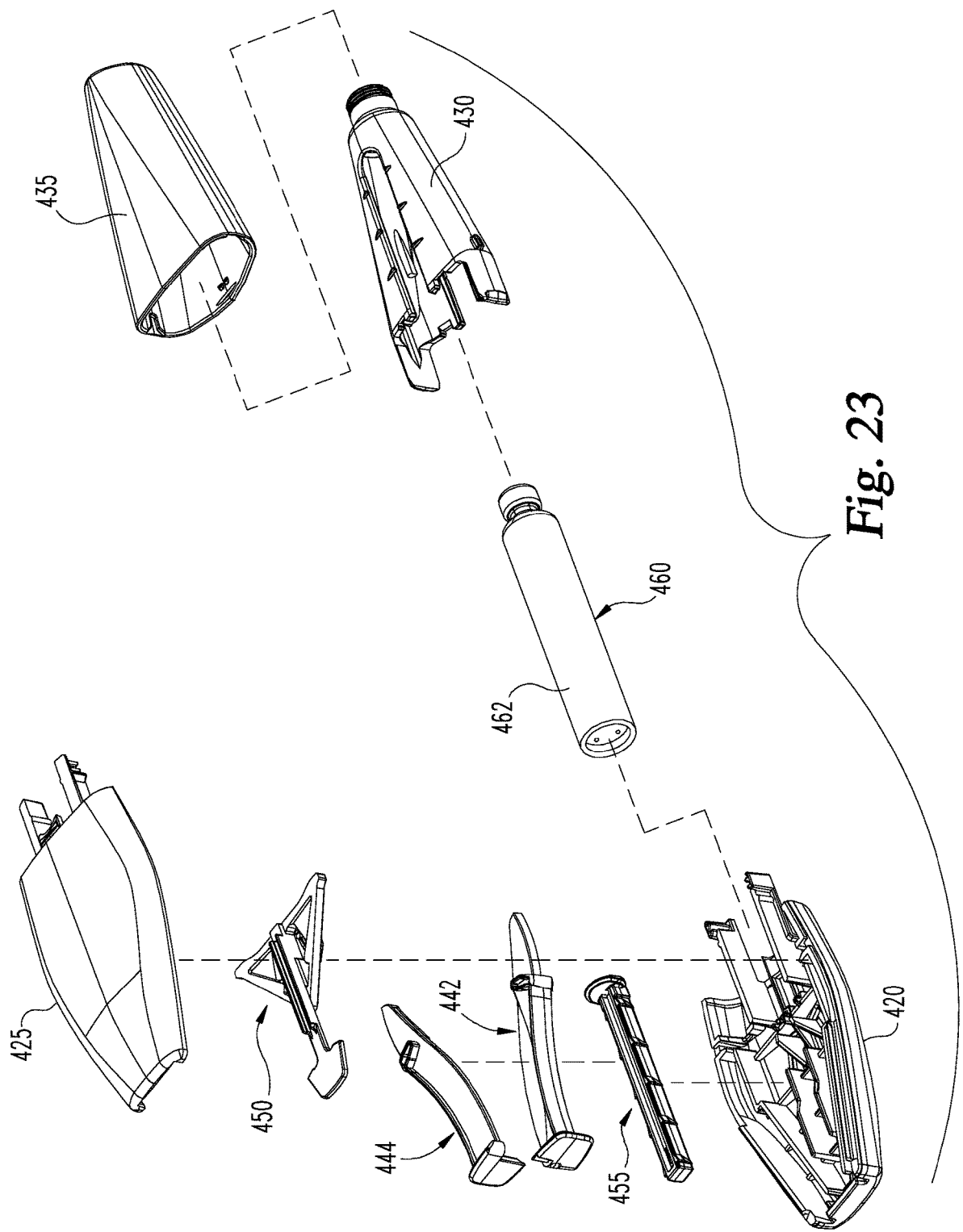
FIG. 23 is an exploded perspective view of the device of FIG. 17.
Figure 24E:
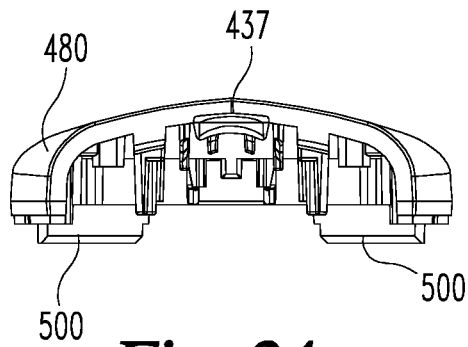
Figure 24D:
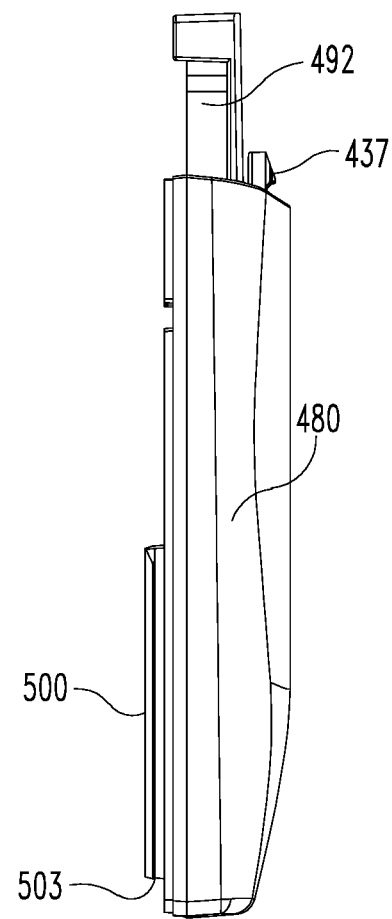
Figure 24F:
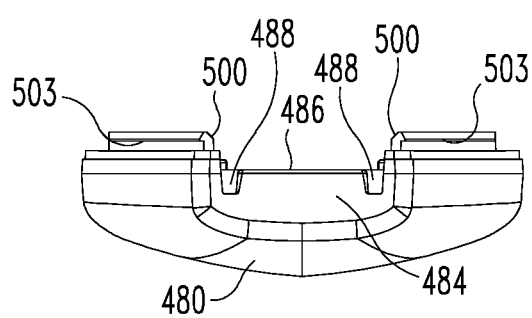
Figure 25C:
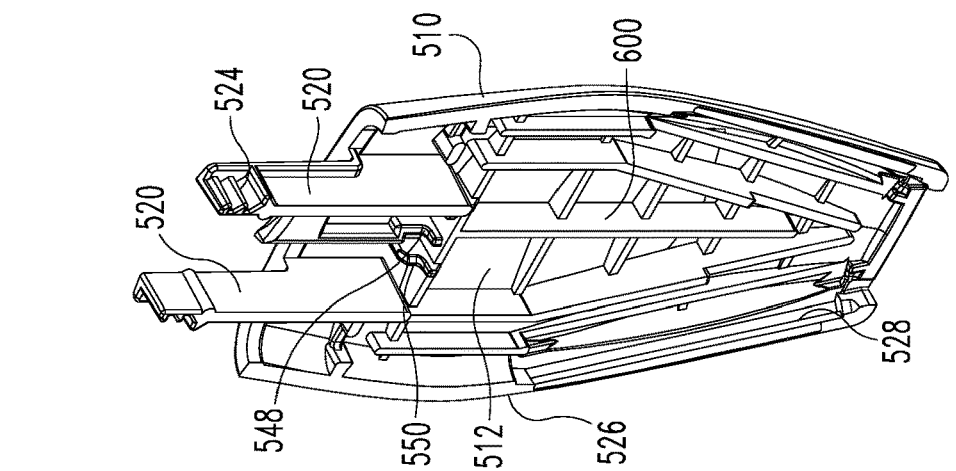
FIGS. 25a, 25b, 25c, 25d, 25e and 25f are a back view, a right perspective view, a left perspective view, a side view, a top view and a bottom view, respectively, of the lid or distal housing front piece of the device of FIG. 17.
Figure 25A:
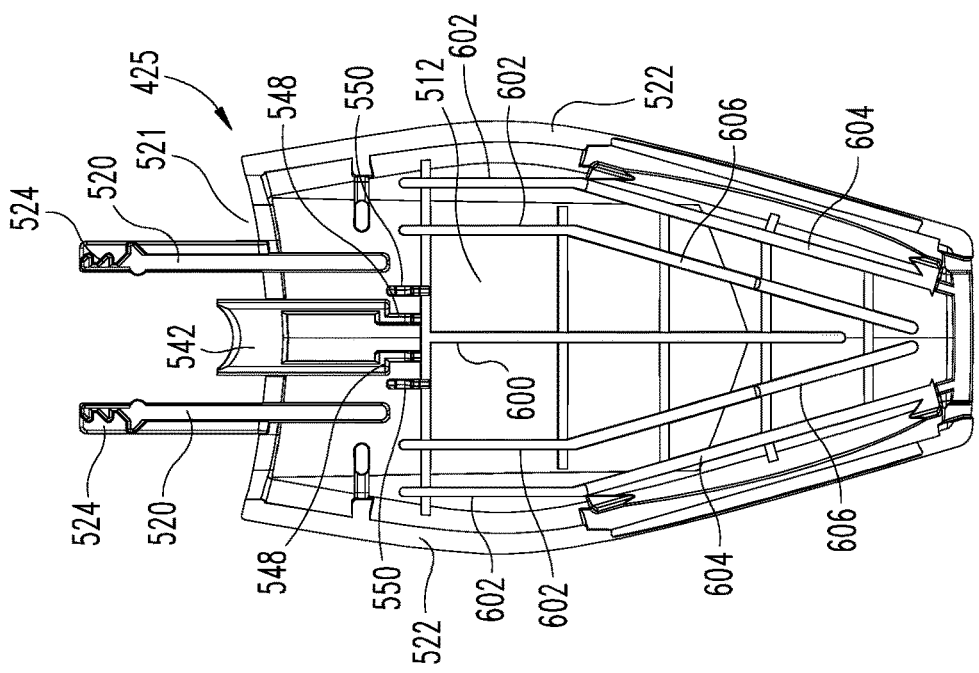
Figure 25B:
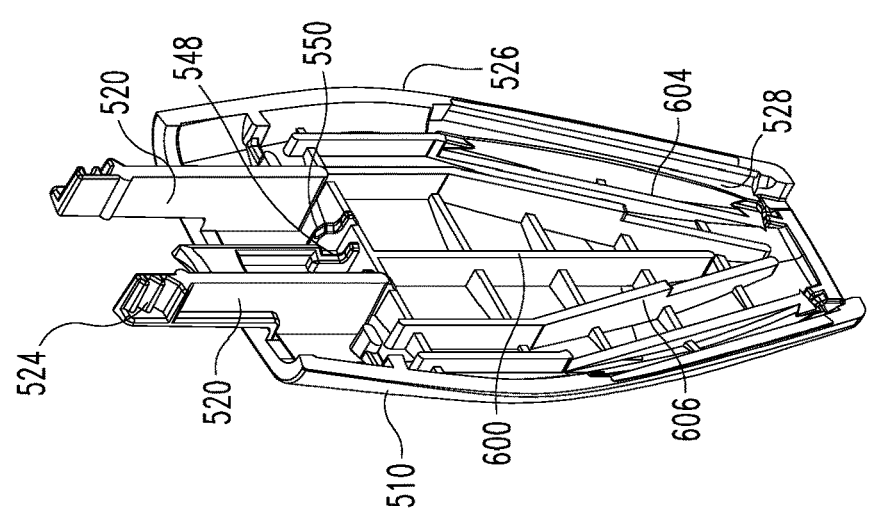
Figure 25E:
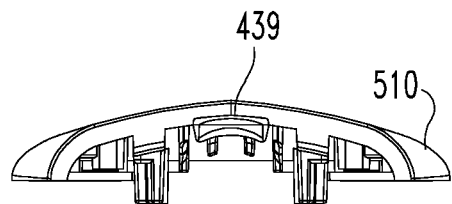
Figure 25D:
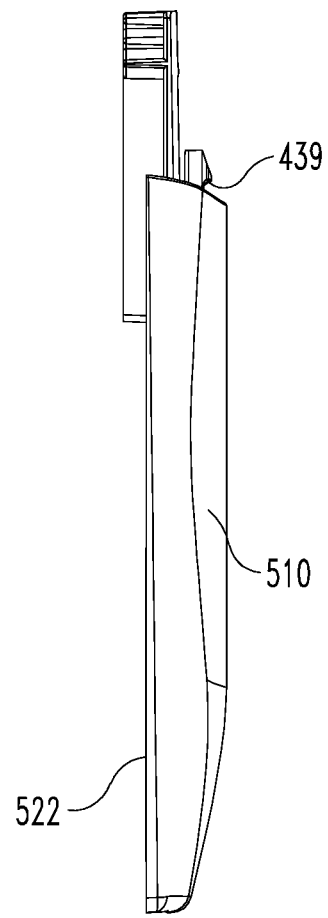
Figure 25F:
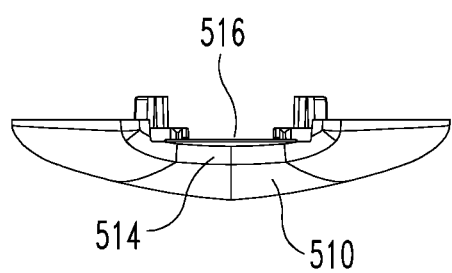
Figure 26C:
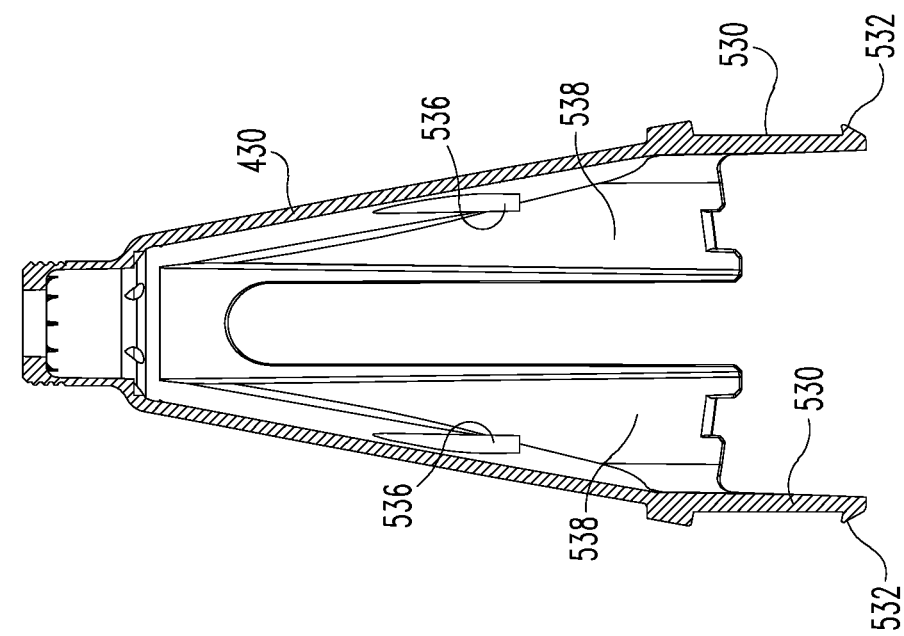
FIGS. 26a, 26b and 26c are a front view, a side view, and a longitudinal cross-sectional view taken along line 26c-26c in FIG. 26b, respectively, of the cartridge holder of the device of FIG. 17.
Figure 26B:
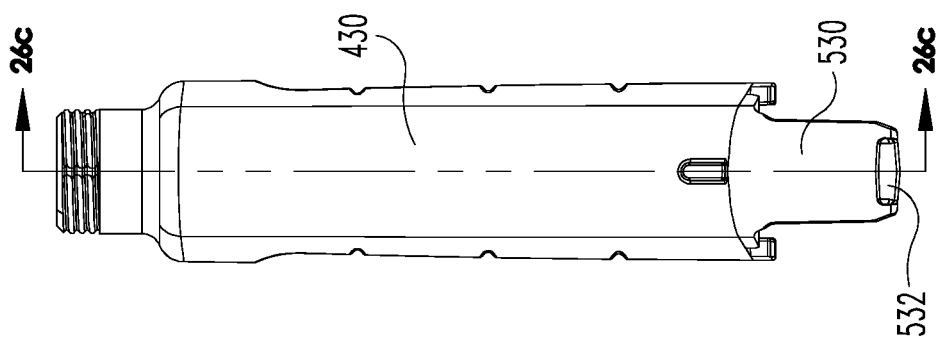
Figure 26A:
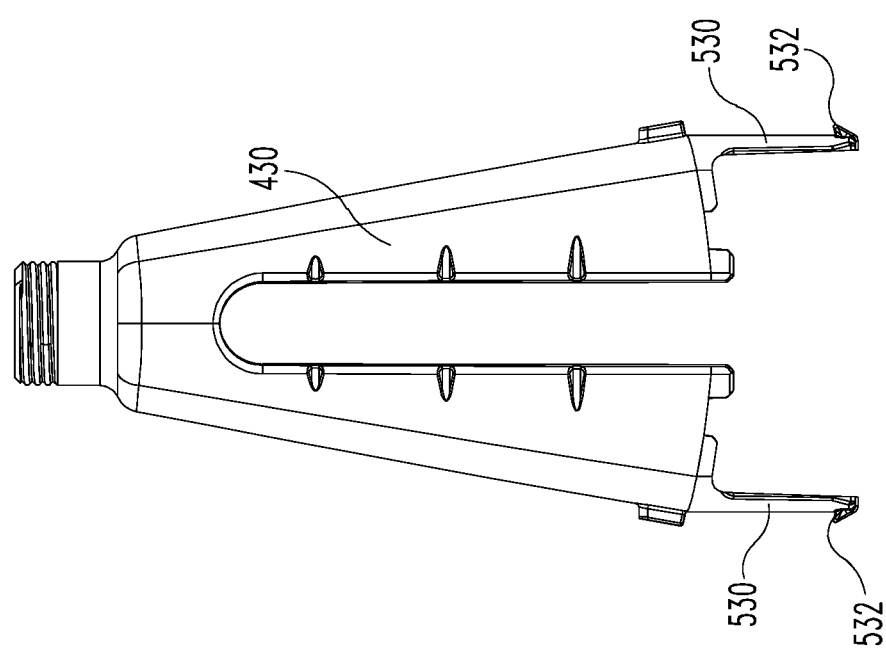
Figure 27A:
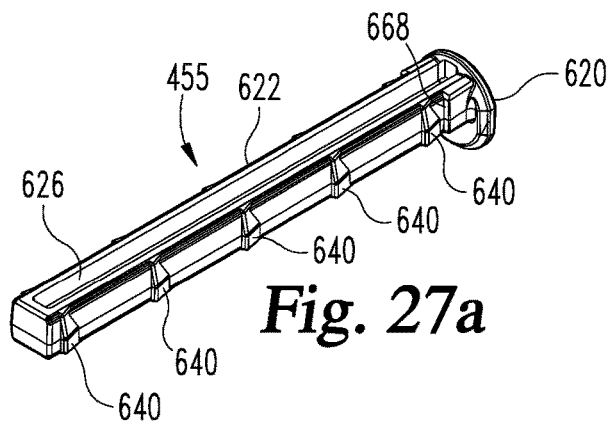
FIGS. 27a, 27b, 27c, 27d and 27e are opposite end perspective views, a side view, a front view, and a cross-sectional view taken along line 27e-27e in FIG. 27c, respectively, of a drive member of the device of FIG. 17.
Figure 27B:
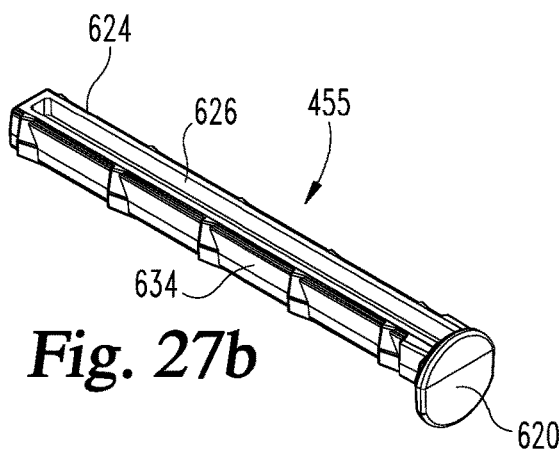
Figure 27C:
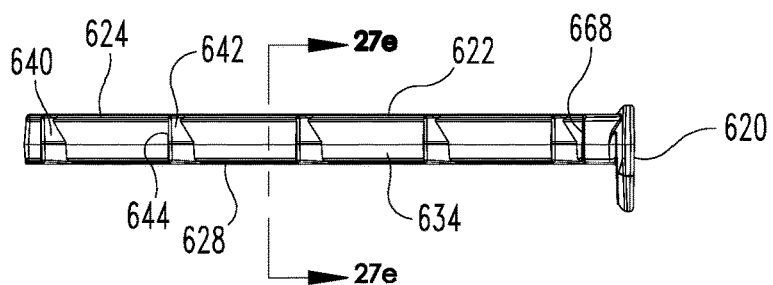
Figure 27D:
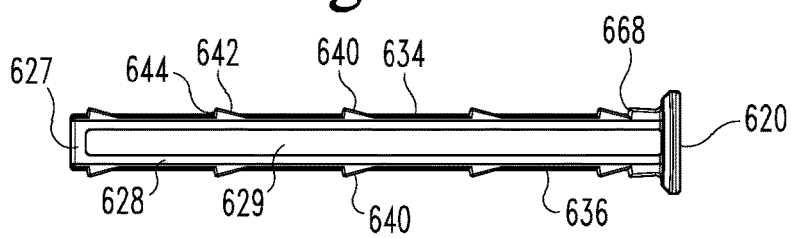
Figure 27E:
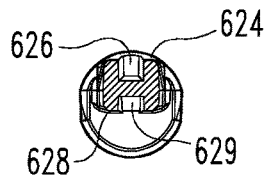
Figure 29A:
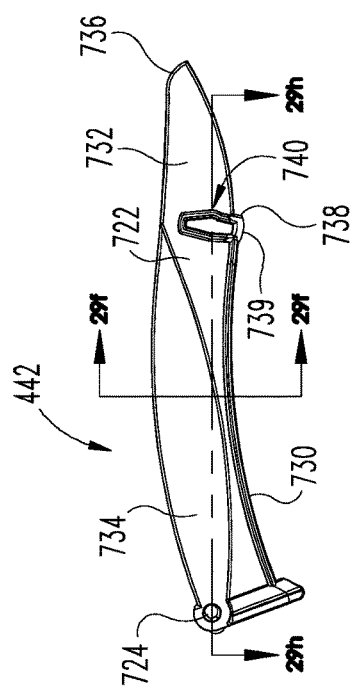
FIGS. 29a, 29b, 29c, 29d, 29e, 29f, 29g and 29h are a front view, four different perspective views, a cross-sectional view taken along line 29f-29f of FIG. 29a, a side view, and a cross-sectional view taken along line 29h-29h of FIG. 29a, respectively, of one plunger arm of the device of FIG. 17.
Figure 29C:
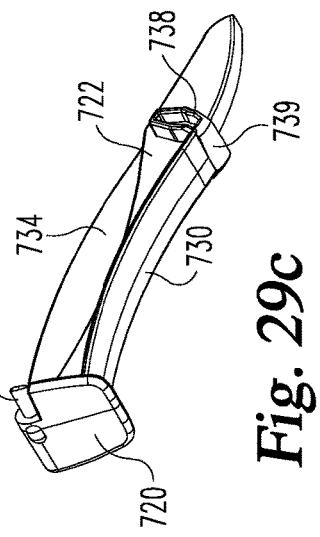
Figure 29B:
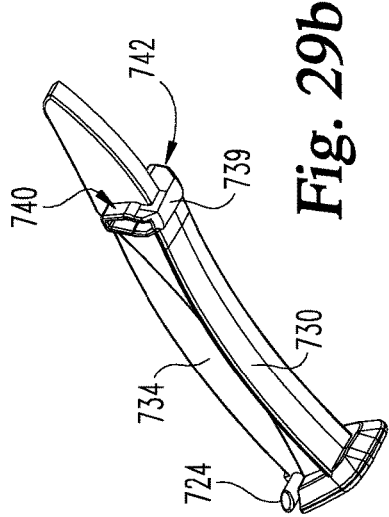
Figure 29D:
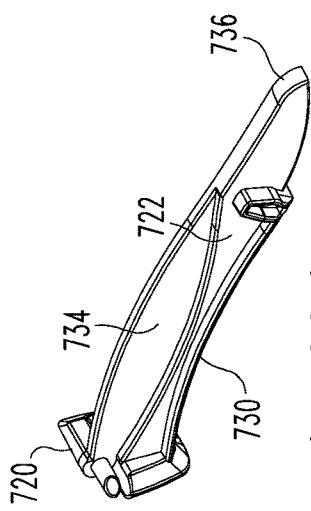
Figure 29F:
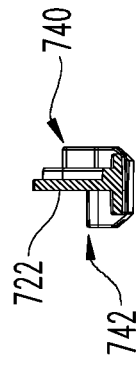
Figure 29H:
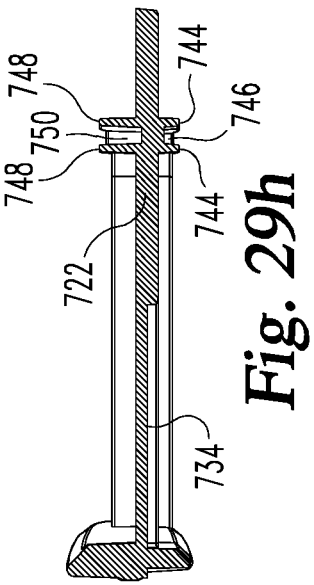
Figure 29E:
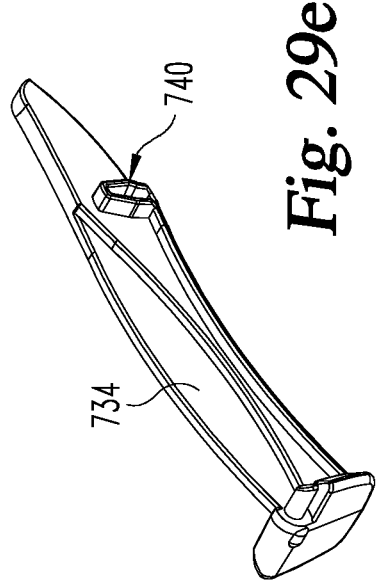
Figure 29G:
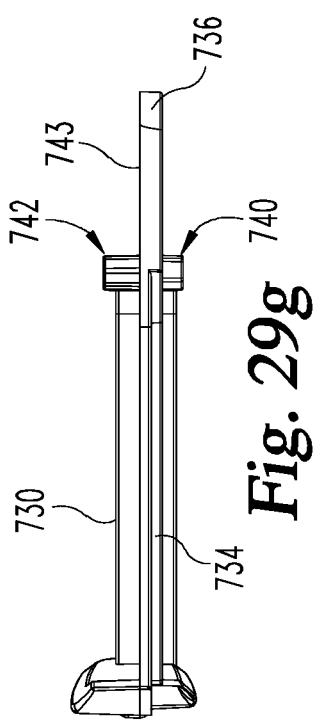
Figure 30C:
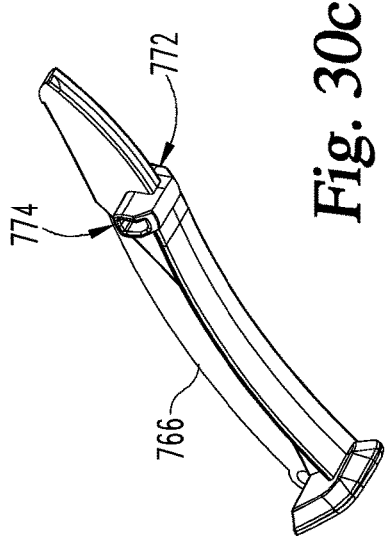
FIGS. 30a, 30b, 30c, 30d, 30e, 30f, 30g and 30h are a front view, four different perspective views, a cross-sectional view taken along line 30f-30f of FIG. 30a, a side view, and a cross-sectional view taken along line 30h-30h of FIG. 30a, respectively, of the other plunger arm of the device of FIG. 17.
Figure 30A:
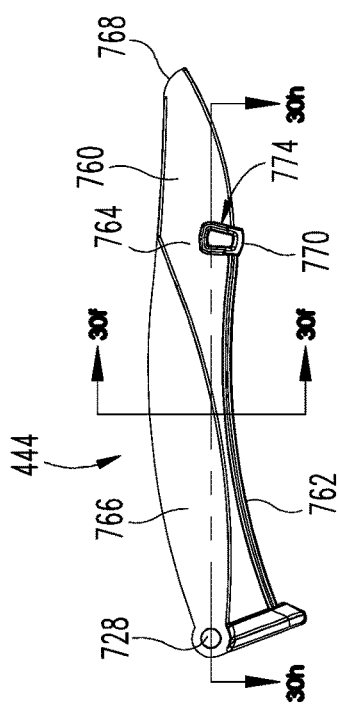
Figure 30D:
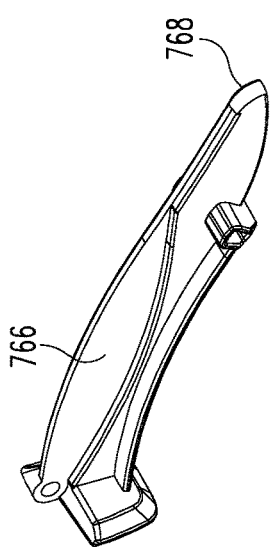
Figure 30B:
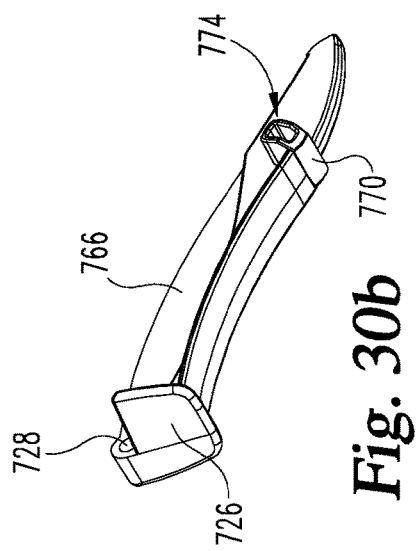
Figure 30F:
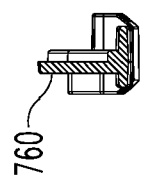
Figure 30H:
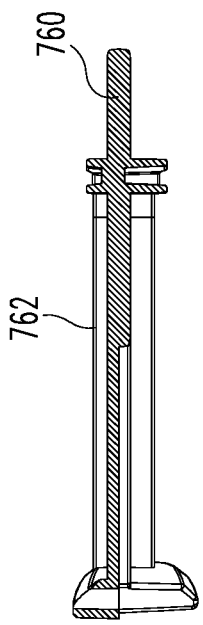
Figure 30E:
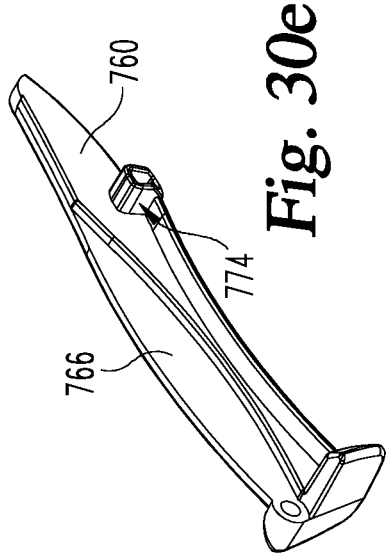
Figure 30G:
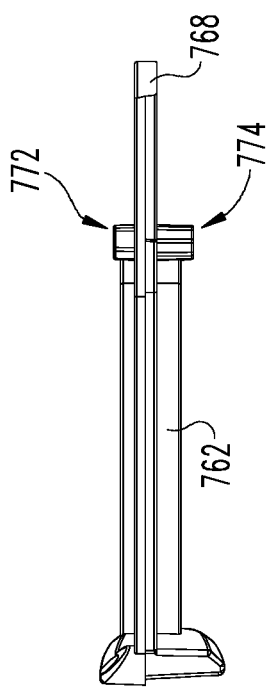
Figure 31A:
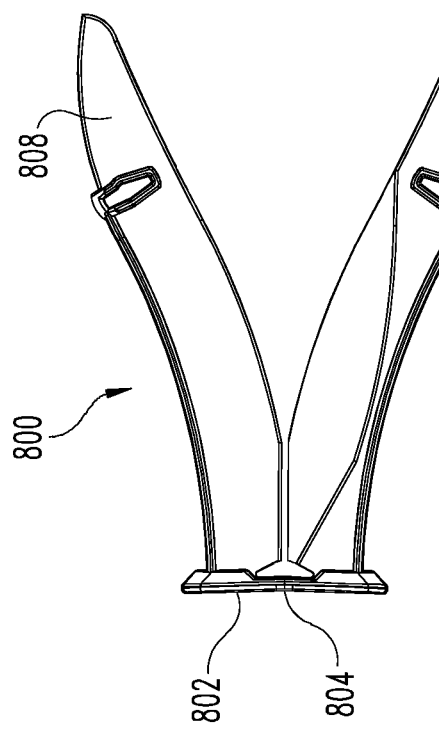
FIGS. 31a, 31b, 31c, 31d, 31e and 31f are a front view, two different perspective views, opposite end views, and a side view, respectively, of a one-piece plunger suitable for use in the device of FIG. 17.
Figure 31C:
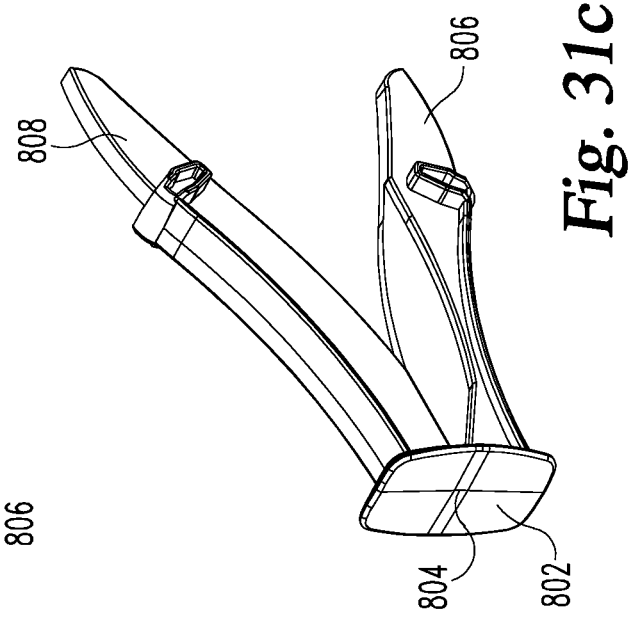
Figure 31B:
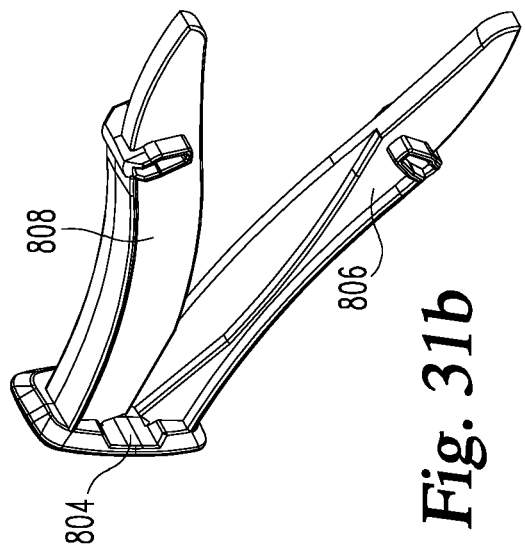
Figure 31E:
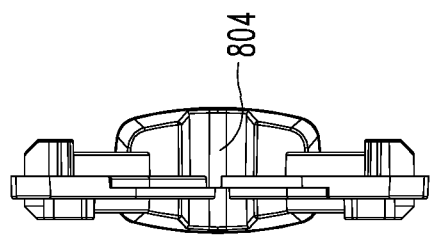
Figure 31D:
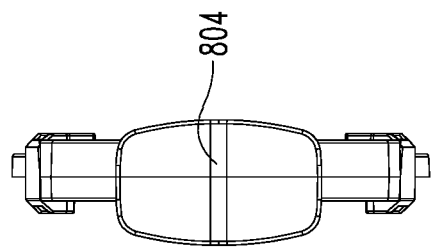
Figure 31F:
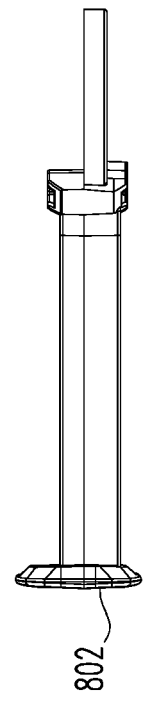

Extending laterally inward from glide 738 is a boss 740 projecting from the forward face 732 of member 722 and a boss 742 projecting from the rearward face 743 of member 722. Boss 740 is formed by a ringing rib 744 with a recessed interior 746 to reduce surface area along its forward face that slides along housing rib 604. Boss 742 is formed by a ringing rib 748 with a recessed interior 750 to reduce surface area along its rearward face that slides along housing rib 580, and as shown in FIG. 21 boss 742 extends lesser laterally inward than boss 740, but with the same mirror image dimensions as boss 774 of plunger arm 444.

Plunger arm 444 is similar in many respects to plunger arm 442 and includes flat member 760 with a flange 762 that slides within a housing notch lobe 488. The rearward face 764 of member 760 includes a scalloped recess 766 that accommodates overlap with plunger arm 442. Member 760 includes a proximal glide 768, a distal glide 770, a forward facing boss 772 and a rearward facing boss 774 that are mirror images of their corresponding components 736, 738, 740 and 742 of plunger arm 442.

The distal edges of boss 740, 772 are shaped to engage pull surfaces 708 to allow the plunger to pull the driver 450 distally during dose preparing.

An alternate plunger of device 400 is shown in FIGS. 31*a*-31*f*. This plunger 800 is formed with a one piece construction. The plunger end plate 802 includes a flexible web hinge portion 804 along its central region that allows the necessary motion of members 806 and 808 relative to each other. In other respects plunger 800 is the same as the plunger formed by the assembly of plunger arms 442 and 444.

From the perspective of a user, the operation of device 400, other than its ready to dispense indication provided by the flag feature of driver tip region 706 is identical to the operation of device 20.

In pertinent part, when the plunger is pulled distally or out from housing 410 by a user gripping the sides of button end plates 720, 726 and then pulling, the driver 400 is eventually pulled distally by bosses 740 and 772 abutting and then pushing distally the pull surfaces 708, all without movement of drive member 455. The distal travel of plunger arms 442, 444 is physically halted by bosses 742, 774 hitting stub walls at distal ends of ribs 580, at which point the device 400 is prepared for dispensing. If the last available dose of medication within device 400 has previously been used, an attempt to prepare device 400 by pulling the plunger sufficiently distally is thwarted by driver boss 677 being stopped upon reaching drive member wall 627.

Figure 32:
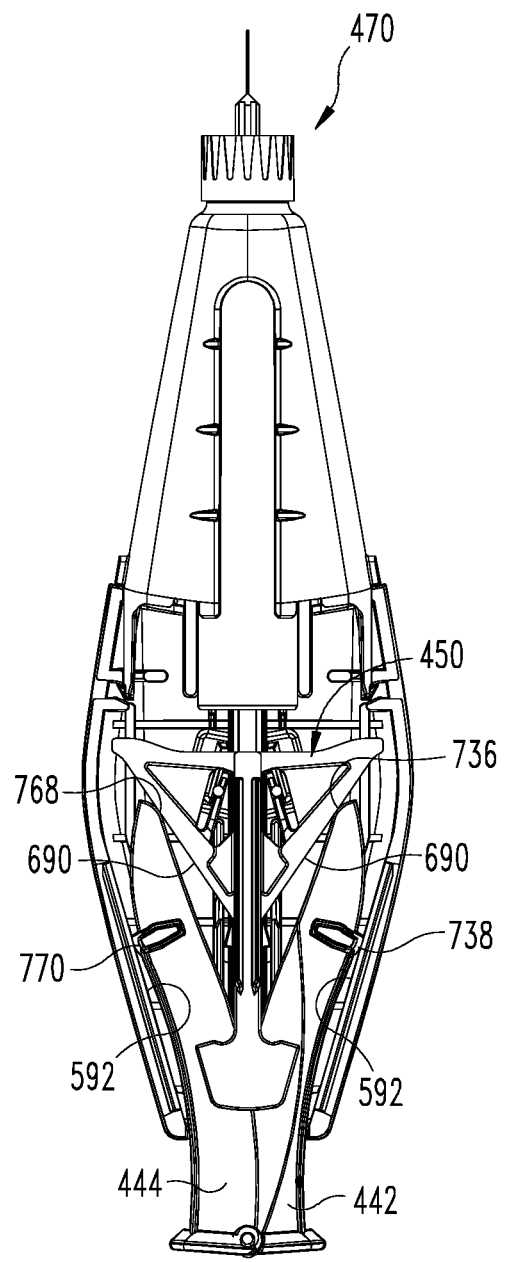
FIGS. 32 and 33 are front and perspective views, respectively, of the device of FIG. 22, and with a needle attached, in the process of being shifted to deliver a previously set dose.
Figure 33:
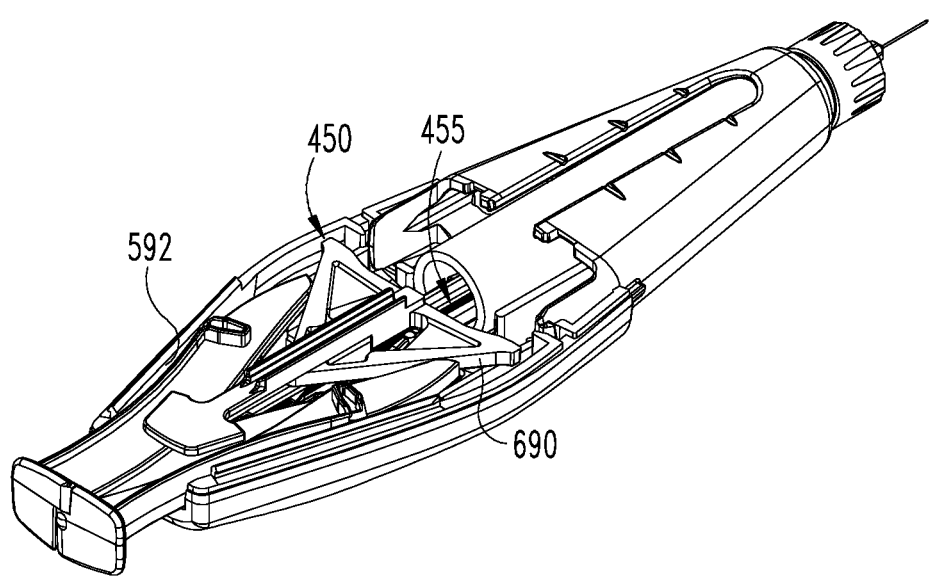

With a prepared device 400, when a user then plunges the plunger by pressing on button end plates 720, 726, the proximal advancement of plunger arms 442 and 444 within housing 410 will cause proximal glides 736 and 768 to move in sliding engagement with driver ramp surfaces 690 and distal glides 738 and 770 to move in sliding engagement with housing ramp surfaces 592. Due to the relationship between the ramp surfaces such motion results in driver 450 and therefore drive member 455 advancing proximally to force medicine through needle assembly 470. FIGS. 32 and 33 illustrate device 400 at this point in the process. The proximal travel of plunger arms 442, 444 is physically halted by bosses 742, 774 hitting stub walls at proximal ends of ribs 580, and after a suitable hold time allowing any compression of the cartridge piston 464 to have subsided, the dose is considered fully dispensed.

Device 400 is well suited for delivering four 0.75 mL doses. By suitably changing the driver 450 and drive member 455, the device can be arranged for other dosage counts and volume, such as 3× 1.0 mL doses to 7×0.42 mL doses.

While this invention has been shown and described as having preferred designs, the present invention may be modified within the spirit and scope of this disclosure. For example, if device 20 were desired to be reusable, provided a manner of attaching a new supply of medicine were provided, the drive mechanism could be made resettable. For instance, to be made so resettable, a manually rotatable collar could be provided that first rotates the drive member within the housing to allow the drive member then to be pushed distally without interference of the pawls 130 and 224, and then rotates the drive member to a pawl engaging position for use again. This application is therefore intended to cover any variations, uses or adaptations of the invention using its general principles. Further, this application is intended to cover such departures from the present disclosure as come within known or customary practice in the art to which this invention pertains.

I claim:

1. A dispensing device for dispensing medication from a medication container, comprising;
   a housing;
   a drive member extending within said housing and engageable with the medication container;
   at least one first ramp surface fixed relative to said housing;
   a driver movable within said housing from a first position to a second position to move said drive member for forcing medication from the medication container, said driver including at least one second ramp surface;
   a plunger including at least one push module movable relative to said housing from a ready position to a plunged position;
   said at least one first ramp surface and said at least one second ramp surface having a complementary configuration to cause said driver to be moved toward said second position by a driving force applied to said at least one second ramp surface by said at least one push module as said at least one push module simultaneously engages both said at least one first ramp surface and said at least one second ramp surface during movement from said ready position to said plunged position, said complementary configuration including converging regions of said at least one first ramp surface and said at least one second ramp surface sized and positioned to prevent said at least one push module from continuing to move toward said plunged position until said driver is moved toward said second position by said at least one push module.

2. The dispensing device of claim 1 wherein said at least one second ramp surface is straight and forms a first angle with a direction that said driver moves when moving from said first position to said second position.

3. The dispensing device of claim 2 wherein said at least one first ramp surface is straight and forms a second angle with the direction that said driver moves when moving said first position to said second position.

4. The dispensing device of claim 3 wherein said first angle is greater than said second angle.

5. The dispensing device of claim 1 wherein said driver includes a hollow in which the drive member extends along an axis, wherein said driver moves in a proximal direction when moving from said first position to said second position, and wherein each of said at least one second ramp surface and said at least one first ramp surface has a proximal end that is farther from said axis than a respective distal end.

6. The dispensing device of claim 5 wherein said at least one first ramp surface comprises first and second ramps disposed in rotational symmetry about said axis, and wherein said at least one second ramp surface comprises third and fourth ramps that are disposed in rotational symmetry about said axis.

7. The dispensing device of claim 6 wherein said first and second ramps are disposed on opposite sides of said axis, and wherein said third and fourth ramps are between said first and second ramps and disposed on opposite sides of said axis.

8. The dispensing device of claim 6 wherein said plunger comprises first and second arms each having a proximal end region and a distal end region, said distal end regions of said first and second arms connected to allow movement therebetween, said proximal end regions of said first and second arms respectively including a first push module and a second push module of said at least one push module.

9. The dispensing device of claim 8 wherein said distal end regions of said first and second arms are pinned together to allow pivotal movement therebetween, and wherein said plunger further comprises a manually operable button attached to said distal end regions.

10. The dispensing device of claim 1 wherein said converging regions exist along at least a majority of a length of each of said at least one second ramp surface and said at least one first ramp surface.

11. The dispensing device of claim 1 wherein said drive member includes a plurality of teeth adapted for driving engagement by at least one pawl of said driver, a spacing between sequential teeth of said plurality of teeth along a length of said drive member corresponding to a distance said drive member is to move to deliver a single dose from the medication container.

12. The dispensing device of claim 1 wherein said at least one push module comprises first and second rollers, said first roller for rolling engagement with said at least one first ramp surface, said second roller for rolling engagement with said at least one second ramp surface.

13. The dispensing device of claim 12 wherein said first and second rollers are mounted for rotation on a common axle.

14. The dispensing device of claim 1 wherein said driver includes at least one retraction arm configured to be engaged by said at least one push module for pulling said driver distally when said plunger is manually pulled from said plunged position to said ready position to prepare the dispensing device to deliver a dose.

15. The dispensing device of claim 1 wherein said at least one push module comprises first and second glides, said first glide for non-rolling engagement with said at least one first ramp surface, said second glide for non-rolling engagement with said at least one second ramp surface.

16. The dispensing device of claim 1 wherein said driver moves in a proximal direction when moving from said first position to said second position, and wherein each of said at least one second ramp surface and said at least one first ramp surface has a proximal end that is farther from a line of travel of said drive member than a respective distal end.

17. The dispensing device of claim 16 wherein said at least one first ramp surface comprises first and second ramps, and wherein said at least one second ramp surfaces comprises third and fourth ramps.

18. The dispensing device of claim 17 wherein said first and second ramps are disposed on opposite sides of said driver, and wherein said third and fourth ramps are between said first and second ramps and disposed on opposite sides of said driver.

19. The dispensing device of claim 17 wherein said plunger comprises first and second arms each having a proximal end region and a distal end region, said distal end regions of said first and second arms connected to allow movement therebetween, said proximal end regions of said first and second arms respectively including a first push module and a second push module of said at least one push module.

20. The dispensing device of claim 19 wherein said distal end regions of said first and second arms are hinged together to allow pivotal movement therebetween.

21. A dispensing device comprising:
a housing;
a container of medication including a piston and an outlet;
a drive member having an end within said container for advancing said piston;
a driver movable within said housing to move said drive member to advance the container piston to force a dose of medication through said outlet;
a manually operable plunger including a user pushable element and at least one push module, said user pushable element disposed outside of said housing, said at least one push module movable within said housing from a ready position to a plunged position when said user pushable element is operated; and
converging ramp means for converting motion of said at least one push module toward said plunged position into driver movement for advancing the container piston, said driver being moved by a driving force applied to said converging ramp means by said at least one push module.

22. The dispensing device of claim 21 wherein converging ramp means includes first and second ramps disposed directly on said housing and said driver respectively.

23. The dispensing device of claim 21 wherein said drive member is disposed along an axis of injection, and wherein said converging ramp means are disposed on the same side of said axis of injection.

24. The dispensing device of claim 23 wherein said driver moves in a proximal direction when moving said drive member to advance the container piston, and wherein said converging ramp means includes first and second ramps, each of said first and second ramps having a proximal end that is farther from said axis of injection than a respective distal end.

25. The dispensing device of claim 24 wherein each of said first and second ramp means are straight.

26. The dispensing device of claim 21 wherein said converging ramp means comprises first and second ramps, and third and fourth ramps, wherein said plunger comprises first and second arms each having a proximal end region and a distal end region, said distal end regions of said first and second arms connected to allow movement therebetween, said proximal end regions of said first and second arms respectively including a first push module and a second push module of said at least one push module, said first push module engaging said first and second ramps and said second push module engaging said third and fourth ramps.

27. The dispensing device of claim 26 wherein said distal end regions of said first and second arms are pinned together to allow pivotal movement therebetween, and wherein said user pushable element is attached to said distal end regions.

* * * * *